(12) United States Patent
Lovmar

(10) Patent No.: US 12,329,913 B2
(45) Date of Patent: Jun. 17, 2025

(54) URINARY CATHETER FOR CONTROLLED DRAINAGE

(71) Applicant: DENTSPLY IH AB, Mölndal (SE)

(72) Inventor: Martin Lovmar, Mölndal (SE)

(73) Assignee: Dentsply IH AB, Molndal (SE)

( * ) Notice: Subject to any disclaimer, the term of this patent is extended or adjusted under 35 U.S.C. 154(b) by 899 days.

(21) Appl. No.: 17/314,876

(22) Filed: May 7, 2021

(65) Prior Publication Data

US 2021/0260333 A1 Aug. 26, 2021

Related U.S. Application Data

(63) Continuation-in-part of application No. PCT/EP2020/085550, filed on Dec. 10, 2020.

(30) Foreign Application Priority Data

Dec. 10, 2019 (SE) .................................. 1951423-1

(51) Int. Cl.
*A61M 25/00* (2006.01)
*A61M 25/01* (2006.01)
*A61M 25/10* (2013.01)

(52) U.S. Cl.
CPC .... *A61M 25/0017* (2013.01); *A61M 25/0045* (2013.01); *A61M 25/0075* (2013.01);
(Continued)

(58) Field of Classification Search
CPC .......... A61M 25/0017; A61M 25/0075; A61M 25/0045; A61M 25/10; A61M 25/003;
(Continued)

(56) References Cited

U.S. PATENT DOCUMENTS

| 3,539,674 A | 11/1970 | Dereniuk et al. |
| 3,642,004 A * | 2/1972 | Osthagen ............. A61M 25/10 604/249 |

(Continued)

FOREIGN PATENT DOCUMENTS

| CA | 2252631 C | 11/2005 |
| WO | 97/39697 A1 | 10/1997 |

OTHER PUBLICATIONS

Office Action dated Jul. 20, 2020 for Sweden Patent Application No. 1951423-1 (8 pages).
(Continued)

*Primary Examiner* — Jessica Arble
*Assistant Examiner* — Hans Kaliher
(74) *Attorney, Agent, or Firm* — SCHWEGMAN LUNDBERG & WOESSNER, P.A.

(57) ABSTRACT

Improved urinary catheters are described. One example urinary catheter includes a catheter shaft with an internal lumen, extending between a distal discharge opening and a proximal drainage opening, arranged at a proximal tip of the catheter shaft. An overcoat layer encircles a portion of the catheter shaft, forming a closed deformable fluid filled cavity intermediate the overcoat layer and the outer surface of the shaft. The overcoat layer is elastically deformable to allow for movement of the fluid within the cavity during deployment. At least a portion at the proximal end is arranged to be compressed to a smaller diameter during insertion, and upon continued insertion of the catheter shaft through the urethra into at least the bladder neck, arranged to expand back toward a greater diameter, as the fluid is caused to flow toward the proximal end of the fluid filled cavity.

16 Claims, 14 Drawing Sheets

(52) U.S. Cl.
CPC ..... *A61M 25/10* (2013.01); *A61M 2025/0024* (2013.01); *A61M 25/003* (2013.01); *A61M 25/0032* (2013.01); *A61M 2025/0035* (2013.01); *A61M 2025/0076* (2013.01); *A61M 2025/0177* (2013.01)

(58) Field of Classification Search
CPC ...... A61M 25/0032; A61M 2025/0076; A61M 2025/0177; A61M 2025/0024; A61M 2025/0035; A61M 2039/248; A61F 2/0009; A61F 2/0022; A61F 2/04; A61F 2002/047
See application file for complete search history.

(56) References Cited

U.S. PATENT DOCUMENTS

| | | | | |
|---|---|---|---|---|
| 4,601,713 | A * | 7/1986 | Fuqua | A61M 25/0032 604/528 |
| 4,932,938 | A * | 6/1990 | Goldberg | A61F 2/0022 604/99.04 |
| 5,114,398 | A * | 5/1992 | Trick | A61F 2/0013 604/249 |
| 5,306,226 | A | 4/1994 | Salama | |
| 5,501,669 | A * | 3/1996 | Conway | A61M 25/10 604/328 |
| 5,624,395 | A * | 4/1997 | Mikhail | A61M 25/0017 604/99.04 |
| 5,749,826 | A * | 5/1998 | Faulkner | A61F 2/0009 604/537 |
| 6,743,208 | B1 * | 6/2004 | Coyle | A61M 25/0075 604/167.03 |
| 7,306,586 | B2 * | 12/2007 | Beaufore | A61M 25/0017 604/533 |
| 2001/0022411 | A1 | 9/2001 | Conway et al. | |
| 2001/0052658 | A1 * | 12/2001 | Conway | A61F 2/0022 264/130 |
| 2004/0260333 | A1 | 12/2004 | Dubrul et al. | |
| 2017/0105826 | A1 * | 4/2017 | Erikstrup | A61M 25/0075 |
| 2020/0230356 | A1 * | 7/2020 | Utas | A61M 25/0045 |

OTHER PUBLICATIONS

International Search Report and Written Opinion mailed Mar. 11, 2021 for International Patent Application No. PCT/EP2020/085550 (13 pages).

* cited by examiner

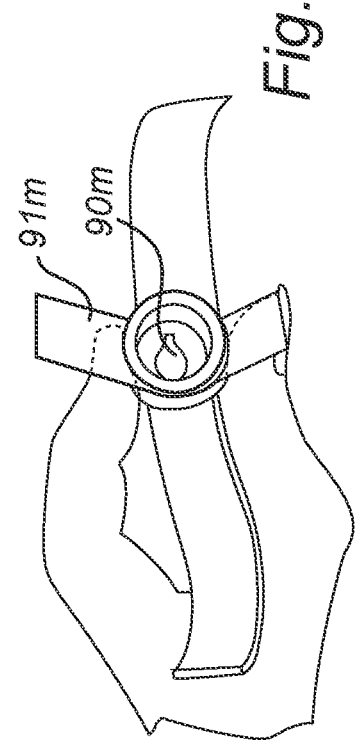
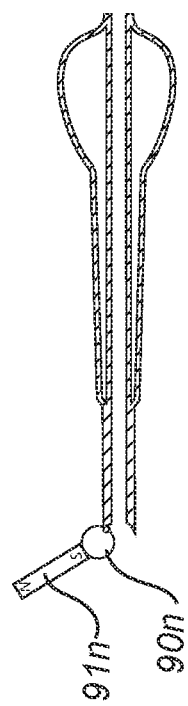
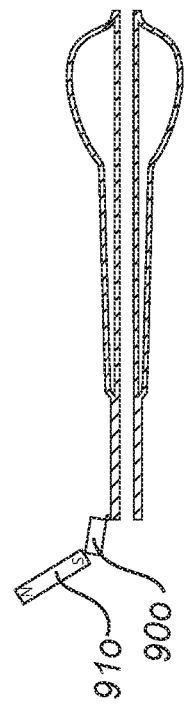
Fig. 23
Fig. 24
Fig. 25
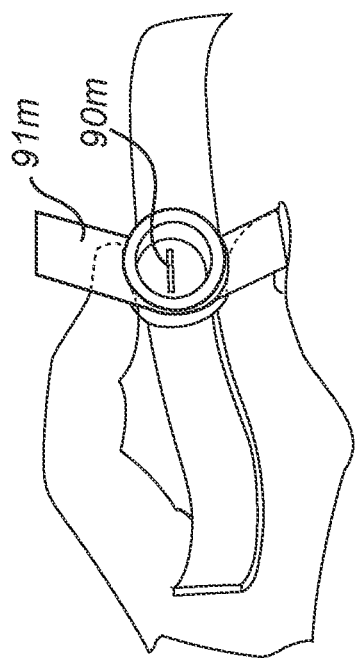
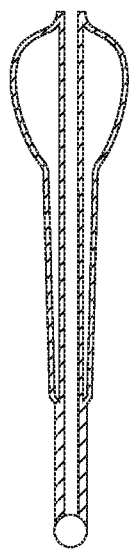
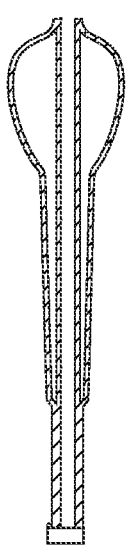

URINARY CATHETER FOR CONTROLLED DRAINAGE

CROSS REFERENCE TO RELATED APPLICATIONS

This application is a continuation in part of and claims priority to International Patent Application No. PCT/EP2020/085550, filed on Dec. 10, 2020, which claims the benefit of priority of Sweden Patent Application No. 1951423-1, filed on Dec. 10, 2019. The entire disclosure of the aforementioned patent applications are incorporated by references as part of the disclosure of this application.

TECHNICAL FIELD OF THE INVENTION

The present invention relates to a urinary catheter, for medium or longtime use, and with controllable drainage.

BACKGROUND OF THE INVENTION

Dysfunction in the detrusor and sphincter muscles can have multiple causes and a number of different symptoms. Common for all urinary disorders is that the storage phase or the voiding phase of the bladder is affected. When a patient has issues with the storage phase it may appear as urinary incontinence while problems with the voiding phase may lead to urinary retention. Thus, incontinence causes leakage in the storage phase, while retention causes inability to void voluntarily and/or residual urine after voiding. These are the most common urinary disorders.

Urinary retention (UR) is a condition where the urinary bladder is unable to void urine completely. This can be caused by blockages of the urethra, nerve problems, medications, overactive sphincter, weakened bladder muscles, or as a side effect to treatment of urinary incontinence. Issues that may cause UR include e.g. prostate enlargement, brain or spinal cord infections or injuries, diabetes, stroke, MS, pelvic injury or trauma, or heavy metal poisoning.

Urinary incontinence (UI) is the involuntary leakage of urine from the urinary bladder. It is a large and ever growing problem, and it is e.g. expected that most women are affected at some point in their life. Urinary incontinence is generally caused by an underactive sphincter, where it cannot contract properly since the sphincter cannot keep tight and leakage may occur. Reasons for having an underactive sphincter could be complex vaginal deliveries, gynecological surgeries, radiation damages, unsuccessful urological procedures, etc. Urinary incontinence can also occur due to having an overactive bladder, which is when nerves send signals to the bladder to micturate at the wrong time.

Known treatments or managements for such urinary dysfunctions comprises incontinence products, such as incontinence pads, catheterization products, stents and surgery.

Many attempts have been made to provide stents and other insertable or implantable products that would be useful for bladder control, to overcome the problems related to UI or UR. For example, WO 97/39697 discloses a single use, disposable urethral plug for use between voidance. This urethral plug comprises a fluid filled retention element, which is compressed during insertion, and which expands in a proximal part once entered into the bladder, to maintain the urethral plug in place. This urethral plug is arranged to block any flow of urine when inserted into place, enabling controlled voiding of urine by removal of the urethral plug. Even though this works well, insertion of a new urethral plug of this kind after every voidance of urine is a cumbersome and tedious process, making this device impractical for many practical use situations.

It is also well-known to use urinary catheters for draining urine from the bladder. Urinary catheters can be of an indwelling type, for long or medium term use, such as hours, days or even weeks, or for intermittent use, whereby the catheters are used for a single draining procedure, typically lasting a few minutes. Urinary catheters are typically used by persons having difficulty to control when to urinate, have urinary incontinence, or have urinary retention. Indwelling urinary catheters, and especially catheters of so-called Foley type, are normally inserted by nurses or other healthcare personnel. Intermittent urinary catheters, on the other hand, are often used for self-catheterization, and individuals who suffer from e.g. urinary incontinence will normally self-catheterize several times a day.

However, catheterization is still a relatively tedious and cumbersome procedure. Further, often users of urinary catheters have limited or diminished dexterity, e.g. as a result of spinal cord injuries, which makes it of further importance to enable as simple catheterization as possible. Also, users of intermittent catheters are often required to self-catheterize outside the privacy of the home, such as in public restrooms.

Thus, for these and other reasons, it is desirable that the catherization can be made by the user him-/herself, and that catheterization and draining of urine can be facilitated even further.

Thus, there is still a need for improved device for urine voidance, and in particular an improved urinary catheter. The urinary catheter should preferably be relatively simple and cost-efficient to produce. Further, the urinary catheter should be easy and intuitive to use, and preferably enable self-catheterization, even for users with reduced dexterity. Thus, there is a general need for a more simplified catheterization procedure.

SUMMARY OF THE INVENTION

It is therefore an object of the present invention to provide a urinary catheter which at least alleviates the above-discussed problems.

This object is obtained by means of a urinary catheter in accordance with the appended claims.

According to the invention, there is provided a urinary catheter for insertion into the urethra comprising:
  a catheter shaft with an outer surface and an internal lumen, extending between a distal discharge opening and at least one proximal drainage opening, arranged at or in the vicinity of a proximal tip of the catheter shaft;
  an overcoat layer encircling at least a portion of said catheter shaft and extending substantially along said catheter shaft, thereby forming a closed deformable fluid filled cavity intermediate said overcoat layer and said outer surface, said fluid filled cavity having a proximal end and a distal end, wherein said overcoat layer is elastically deformable to allow for movement of said fluid within said cavity during deployment, wherein the fluid filled cavity is arranged to deform upon insertion of said catheter shaft into the urethra, whereby at least a portion of said fluid filled cavity at said proximal end is arranged to be compressed to a smaller diameter, and upon continued insertion of said catheter shaft through the urethra into at least the bladder neck, at least said portion of said fluid filled cavity at said proximal end being arranged to expand back toward a greater diameter, as the fluid of the fluid filled cavity at said distal end is caused to flow toward the proximal end of the fluid filled cavity;

a valve arranged to set the internal lumen of the catheter shaft in an open or closed state; and a valve handle or actuator arranged to bring the valve to an opened state upon activation.

The terms "proximal" and "distal" are here used to disclose positioning relative the orientation of the urinary catheter, where "proximal" is used for a position closest to the body, or farthest inserted into the body, whereas "distal" indicates a position less close to the body, or not as far inserted into the body. Thus, "proximal" generally refers to a position closer to the insertable end, the insertion tip, whereas "distal" generally refers to a position closer to the rearward end, i.e. the discharge outlet.

This urinary catheter has many advantages. The catheter is preferably a disposable, intended for a single use, but can be used continuously for a relatively long time, such as for one or several hours, or even for longer time periods, such as one or several days, or even for one or several weeks, or one or several months. The valve, when in the closed state, efficiently prevents urine from exiting the bladder, and allows controlled drainage of urine when in the open state. When intended for use for longer time periods, the catheter may further be provided with antibacterial properties, such as an antibacterial external surface, to prevent urinary tract infections and the like.

The overcoat layer is preferably thin enough to allow a small diffusion of the fluid out from the fluid filled cavity, through the overcoat layer. This is of advantage, since it will provide a small amount of the fluid, such as oil, on the external surface of the overcoat layer. This provides some lubrication to the catheter surface, which will facilitate insertion and withdrawal of the catheter into and out from the urethra.

In such cases, where the overcoat layer allows a small diffusion of the fluid out from the fluid filled cavity, through the overcoat layer, it is also possible to add an antibacterial agent to the fluid inside the fluid filled cavity. Due to the diffusion, this antibacterial agent will then be diffusing out from the fluid filled cavity, together with the fluid, such as oil, thereby providing an antibacterial effect on the outer surface of the catheter.

The urinary catheter is also easy to insert and remove, and requires minimal user skill for insertion and removal. In particular, it requires no filling of any balloon or the like, as in conventional Foley catheters. There is also no risk of hazardous overfilling of the balloon, etc. There is also no risk of accidentally forgetting to deflate the balloon prior to extraction, since the retention element of the present invention does not need to be actively deflated. It is, thus, very useable for self-catheterization, and can easily be used also for users having limited dexterity.

In addition, the catheter can be manufactured at a low cost.

The urinary catheter is particularly suitable for female users, as a female urinary catheter, even though it can also be used for male users, as a male urinary catheter.

The retention mechanism of the urinary catheter is preferably similar to the retention mechanism used in the urethral plug disclosed in WO 97/39697, said document hereby being incorporated in its entirety by reference. The catheter is designed to exert a pressure in response to that of the structures of the urinary tract, such that the catheter can be easily removed from the urinary tract, and ultimately the body, by the user by pulling it outwards, thereby manually initiating deformation of the device.

In human females, the urethra is relatively flat in cross-section when in its normal undilated state. Upon dilation, such as the passage of urine during voidance, the urethra takes a rounded ovular or flattened tube shape, and expands such that the cross-sectional diameter increases. It is this undilated diameter of the urethra that will be referenced throughout this application as the "diameter", for purposes of uniformity, as it is well known that the urethra can be dilated into many cross-sectional shapes of varying diameter.

The catheter is such that it is typically of a shape with a portion thereof having a diameter greater than that of an undilated urethra, but can be deformed by urethral wall pressure such that the diameter changes at various points along the urinary tract, for insertion, deployment and removal therefrom.

The catheter is small and comfortable to use. In use, the external part of the catheter, i.e. the part which is maintained outside the urethra, can be made very small, thus allowing the catheter to be essentially unnoticeable, even when the user wears tight clothing. The external part is further preferably arranged to enable connection to external parts, such as an extension tube or a urine collection bag.

The transurethral part of the catheter, i.e. the part of the catheter which is to be within the urethra during use, may be provided with a hydrophilic surface coating, or other coatings which reduces friction during insertion. Alternatively, a lubricant, such as a gel, may be used.

The proximal part of the catheter, i.e. the part which is inserted into the bladder during use, is preferably arranged to securely retain the catheter in position, and is also provided with the proximal drainage opening(s) to allow urine to be drained through the catheter when the valve is opened.

The valve is preferably arranged so that it is easily accessible. Further, the handle/actuator is preferably able to be manipulated with only one hand, and in an intuitive manner, so that the user need not see the handle/actuator during the manipulation. The valve is further preferably sufficiently leakproof, ensuring that urine is not leaking out when the valve is closed.

The catheter preferably has a length which is longer than the length of the urethra. The female urethra is typically 3-5 cm in length. The catheter, when intended for female use, preferably has a length exceeding 4 cm, and preferably exceeding 5 or 6 cm. Of the insertable length, excluding the length of the external part intended to remain outside the urethra and bladder during use, it is preferred that the part intended to be in the bladder constitutes less than ⅓ of the insertable length, and the part intended to remain in the urethra constitutes more than ⅔ of the insertable length. The external part preferably constitutes 5-25% of the total length, and preferably 10-20%.

When used as a male catheter, the catheter shaft may have a length exceeding 30 cm, or even longer. For male catheters, the overcoat layer may have the same dimensions as for a female catheter, but may also be longer.

The closed cavity is filled with a fluid, which may be a gas, such as air, or a liquid. In a preferred embodiment, the closed cavity is filled with a liquid, such as oil. Itis also feasible to use a mixture of gas and liquid, a gel and the like. The fluid may also comprise an antibacterial agent.

In an embodiment, the at least one proximal drainage opening is arranged farther from said distal discharge opening than said proximal end of the deformable fluid filled cavity. Thus, in such embodiment, one or more drainage opening(s) may be arranged in the side wall of the catheter shaft, between the proximal end of the deformable fluid filled cavity and the proximal tip of the catheter shaft. Additionally, or alternatively, a drainage opening may also be provided at the tip, thereby forming a non-closed tip.

In another embodiment, the at least one proximal drainage opening may be arranged at a part of said catheter shaft over which said overcoat layer extends. To this end, a part of the deformable fluid filled cavity in the vicinity of the proximal end may have a non-circular cross-section, e.g. shaped as a four-leaf clover, forming indentations or vales in which one or more drainage openings may be provided.

In one embodiment the valve is arranged to remain open when the valve actuator or handle is in a first state, and to remain closed when the valve handle or actuator is in a second state. This facilitates drainage, since the valve handle/actuator need only be operated once to open the valve, and then once again for closing the valve after voidance.

In another embodiment, the valve may be arranged to remain closed as a default, and to be opened only when the valve handle or actuator is continuously activated, and to resume its closed state when activation of the valve handle or actuator ceases. This has the advantage that there is no risk of accidentally forgetting to close the valve after voidance. It also functions as a dead-mans-handle, whereby the valve will automatically resume its closed state if the user e.g. looses control of the valve handle/actuator.

In one embodiment, the valve is arranged at or in the vicinity of the distal discharge opening. For example, the valve can be arranged in a part of the catheter which is intended to remain outside the urethra in use. Hereby, the valve can be allowed to have somewhat greater dimensions, such as dimensions exceeding the diameter of the urethra, which facilitates manufacturing. Such a valve is also more easily accessible by the user.

In another embodiment, the valve is arranged at or in the vicinity of the proximal drainage opening. For example, the valve may be arranged in a part of the catheter intended to be inside the bladder during use, and preferably in a part of the catheter shaft extending proximally beyond the proximal end of the fluid filled closed cavity. Hereby, the parts extending out from the urethra when the catheter is inserted into its use position can be minimized, which makes the catheter more discrete, and more comfortable for the user.

The catheter shaft preferably has a Shore A hardness in the range of 70-95, and preferably 75-95, and more preferably in the range 75-85 and most preferably in the range 78-82. Hereby, it is ensured that the shaft maintain is tubular structure even in use, when inserted into the urethra, thereby allowing unrestricted flow and sufficient drainage capacity during voidance. The catheter shaft having such a hardness allows the catheter to be inserted into the urethra without the use of a separate insertion aid.

The overcoat layer is preferably much more flexible than the catheter shaft, and may have a Shore A hardness lower than that of the catheter shaft. In an embodiment, the overcoat layer may have a Shore A hardness in the range of 20-50, and preferably 25-40, and more preferably 25-35, such as about 30.

An enlarged rearward part, functioning as a stopper member, arranged at the distal end of the shaft, as discussed in more detail in the following, may have a Shore A hardness which is higher than that of overcoat layer, and lower than that of the catheter shaft. The enlarged rearward part may have a Shore A hardness in the range of 40-70, and preferably 40-60, and more preferably 45-55, such as about 50.

In one embodiment, the valve is controllable with a handle, which is non-removably connected to the valve. The handle may e.g. be provided in the form of tabs connected to the valve, a circumferential gripping surface surrounding the valve, strings or lever arms connected to the valve, a rotatable handle, a linearly displaceable handle, a push or pull button, and the like. Since the handle is non-removable connected to the valve, there it will always be conveniently at hand, and without any risk of loosing or misplacing it.

In another embodiment, the valve is controllable by an actuator. In embodiments, the actuator may be arranged to engage with the valve for controlling it, wherein the actuator is separably connectable to the valve. For example, the actuator may be in the form of a pin, rod or tube insertable into the catheter for manipulation of the valve, e.g. by pushing the lips of a duck-bill valve apart. Other types of actuators may also be used, such as forceps or the like.

In other embodiments, the actuator may be arranged to control the valve from a remote position, without physical contact. For example, the valve may comprise a ferromagnetic material, to be displaced by an actuator in the form of a magnet.

In an embodiment, the catheter shaft comprises a closed proximal tip. This makes the catheter easier to insert, both since the tip may then be shaped to facilitate insertion, such as being rounded, tapering or the like, and since it facilitates insertion with the aid of an insertion aid, such as a stylet, which may then be inserted into the lumen of the catheter to aid during the insertion procedure. However, a non-closed tip, i.e. a tip with a central opening, may also be used, and may still allow insertion with insertion aids such as stylets.

In embodiments, the valve may be one of: a ball valve, a pinch valve, an umbrella valve, and a duckbill valve.

A ball valve is a form of quarter-turn valve which may use a hollow, perforated and pivoting ball to control flow through it. It is open when the ball's hole is in line with the flow and closed when it is pivoted 90-degrees by the valve handle. The ball need not be spherical, but may instead be e.g. cylindrical.

A pinch valve employs an elastic tubing, and a device that directly contacts the tubing and which may be moved to a clamping position. Forcing the tubing together will create a seal.

A duck bill valve act as backflow prevention devices or one-way valves. They have elastomeric lips in the shape of a duckbill which prevent backflow and allow forward flow. In embodiments of the presently disclosed urinary catheter, the duckbill valve is used as a controllable valve, using its abilities to close automatically, but being able to be opened at will, e.g. by pulling, pushing or squeezing the duckbills apart, by insertion of an actuator into the duckbill, and the like.

In particular, the handle for operating the duckbill valve may be provided in the form of two tabs, extending distally from the duckbill valve on opposite sides thereof. The tabs are preferably of a relatively flexible material, and may in use be pulled apart, thereby opening the duckbill valve. When not in use, the tabs may be arranged to stick together, thereby forming an additional closure of the valve. The tabs may also be connected at their distal ends, thereby forming a loop around the duckbill valve. This simplifies manipulation, and in particular manipulation with only one hand, since the manipulation can then e.g. be made by simply inserting two fingers in the loop and move them apart.

An umbrella valve is a valve that has a diaphragm shaped or umbrella shaped sealing disc. The disc prevents flow in one direction when not actively lifted, but allows flow in the same direction when the disc is lifted up from the opening. The disc may preferably be convex.

In an embodiment, the catheter shaft additionally comprises an enlarged rearward part, a stopper member, at the distal end of the shaft, the stopper member having a diameter greater than the diameter of the shaft. The stopper member and the shaft are preferably integral. The stopper member prohibits to deep insertion into the urethra, and may also serve as a handle, for pulling the catheter out from the urethra when it is to be removed.

The valve, together with the optional handle(s), may be formed as a separate part, and be attached, and preferably non-releasably attached, to the catheter shaft and/or the enlarged rearward part, e.g. by means of adhesive, a friction fit, press fit, or the like.

In particular for female catheters, the valve and/or the enlarged rearward part may be arranged laterally displaced relative to the axial direction of the catheter shaft. Hereby, the catheter may be arranged to that valve and/or the enlarged rearward part extend more rearwardly from the urethral opening than forwardly, i.e. more towards the vagina than towards the clitoris. This provides increased comfort for the user, and also makes it easier to discharge the urine downwardly during discharge of urine.

The catheter may further comprise an insertion aid, such as a stylet, which is removably attachable in the interior lumen of the catheter shaft. The insertion aid preferably has a length greater than the length of the internal lumen.

Preferably, the proximal end of the shaft and the distal end of the shaft extend beyond the overcoat layer.

In one embodiment, the overcoat layer proximate to the proximal end of the shaft includes a first portion, said first portion corresponding to a first portion of said closed cavity having a first volume, and a second portion, said second portion corresponding to a second portion of said closed cavity having a second volume, said first volume and said second volume being variable during deployment. Preferably, the first portion has a bulbous shape and the second portion has a generally cylindrical shape. Preferably, the maximum diameter of the first portion, when in a relaxed state, is greater than the maximum diameter of the second portion, when in a relaxed state, and preferably at least 25% greater, and more preferably at least 50% greater. Further, when in the relaxed state, the first volume may be greater than the second volume. However, alternatively, the first volume may be about the same as the second volume, and in some embodiments, the second volume may be greater than the first volume.

It is further preferred that the catheter has a radiation resistance such that it can endure at least 25 kGy, and preferably at least 50 kGy, essentially without degradation. Hereby, radiation sterilization of the medical device can be used, without affecting the properties of the medical device.

BRIEF DESCRIPTION OF THE DRAWINGS

For exemplifying purposes, the invention will be described in closer detail in the following with reference to embodiments thereof illustrated in the attached drawings, wherein like reference numbers are used to identify corresponding or similar components, wherein:

FIGS. 22-28 are views, some in perspective (FIGS. 23, 28) and some at least partly in cross-section (FIGS. 22, 24-27), of catheters in accordance with further embodiments of the present invention, illustrating different types of valves arranged in a distal, rearward part of the catheter;

DETAILED DESCRIPTION OF PREFERRED EMBODIMENTS

Figure 1:
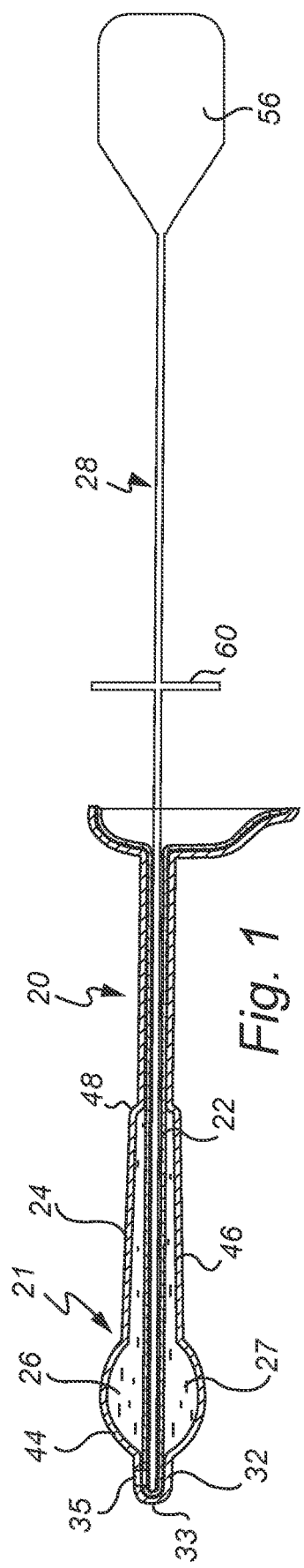
FIG. 1 is a cross sectional view of an embodiment of a catheter in accordance with the present invention.
Figure 2:
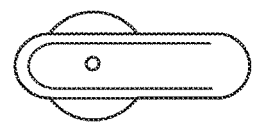
FIG. 2 is a view from the distal end of the embodiment of FIG. 1.
Figure 4:
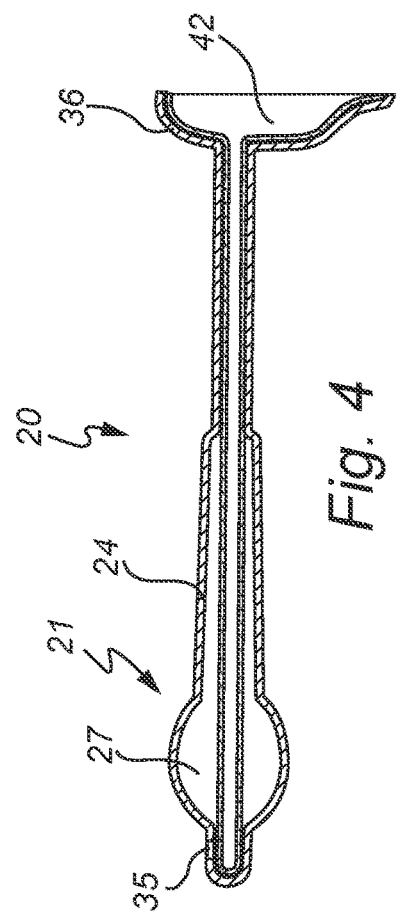
FIG. 4 is a cross sectional view of the embodiment of FIG. 1 with a stylet removed therefrom.
Figure 3:
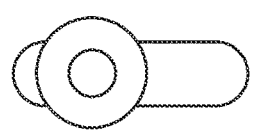
FIG. 3 is a view from the proximal end of the embodiment of FIG. 1.

In the following detailed description preferred embodiments of the invention embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the invention, e.g. the length of the catheter and its various prats, etc.

A catheter in accordance with an embodiment is illustrated in FIGS. 1-4. The catheter 20 comprises a catheter shaft 22. A deformable body member 21, functioning as a retention element, is formed by the catheter shaft 22 and an overcoat layer 24, encircling the catheter shaft 22 along a part of its length, or along its entire length. The length of the overcoat layer 24 is preferably selected to provide a sufficient length for the fluid enclosed therein to be adequately distributed during insertion and extraction (see further below), and with a sufficiently small diameter.

The space between the catheter shaft 22 and the overcoat layer 24 defines a cavity 26, in which fluid 27, such as oil, is encased. The catheter 20 preferably also includes a removable stylet 28, received within the inner lumen of the catheter shaft 22, for deploying the catheter 20 in the urinary tract.

Figure 5:
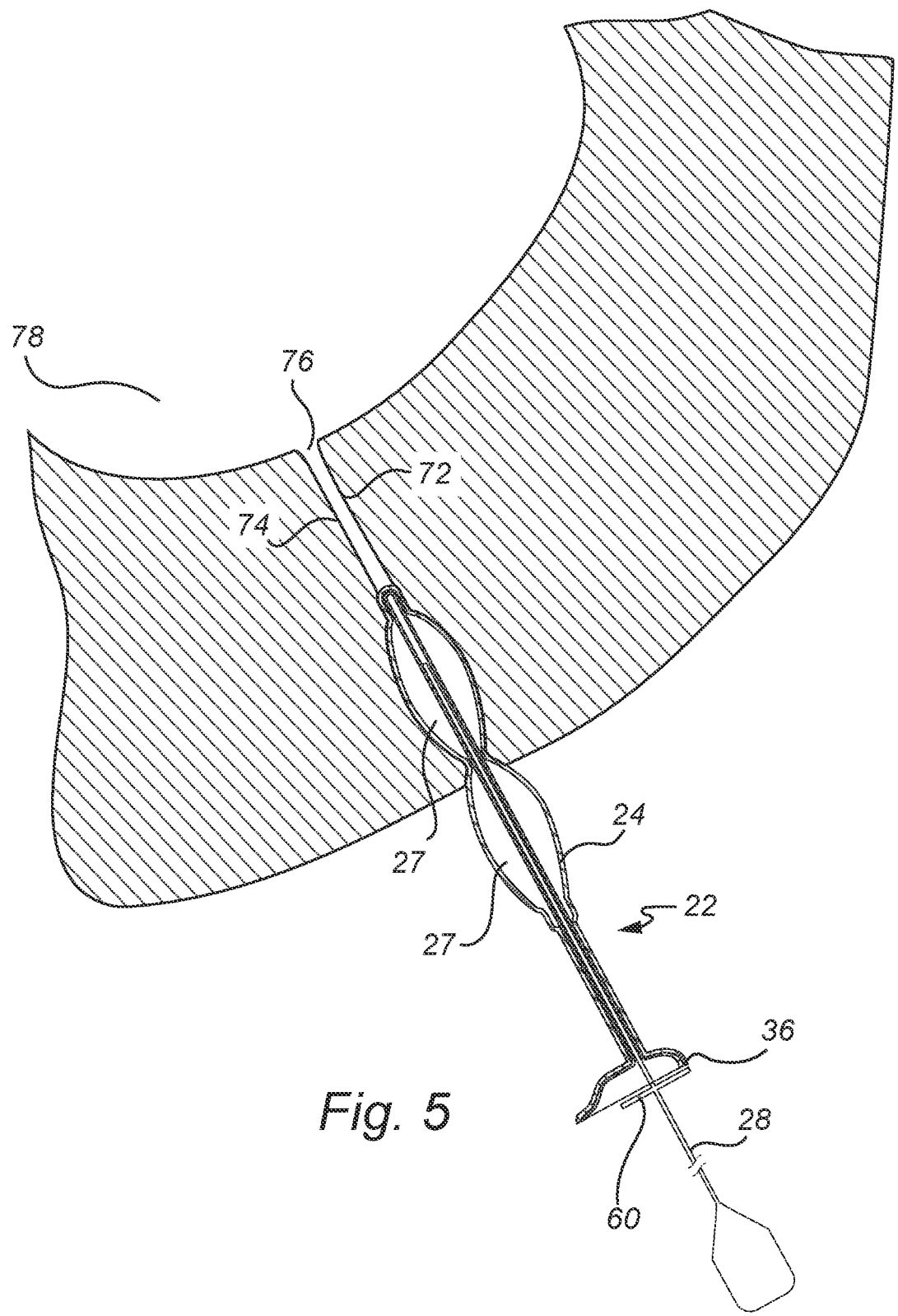
FIGS. 5-7 are cross sectional views of the catheter of the embodiment in FIG. 1 in use upon insertion into the urinary tract of a human female, upon deployment into the urinary tract of a human female, and upon removal from the urinary tract of the human female, respectively.
Figure 6:
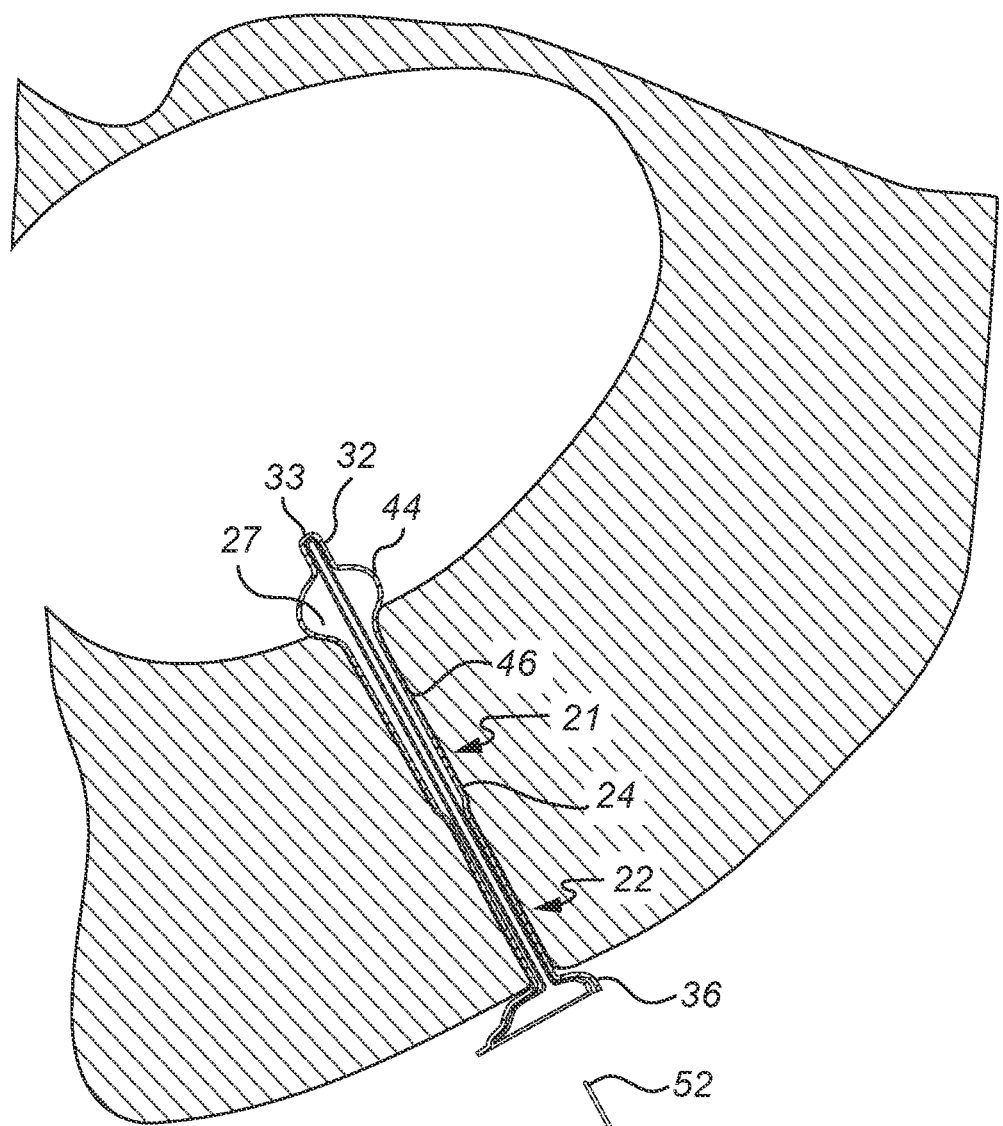
Figure 7:
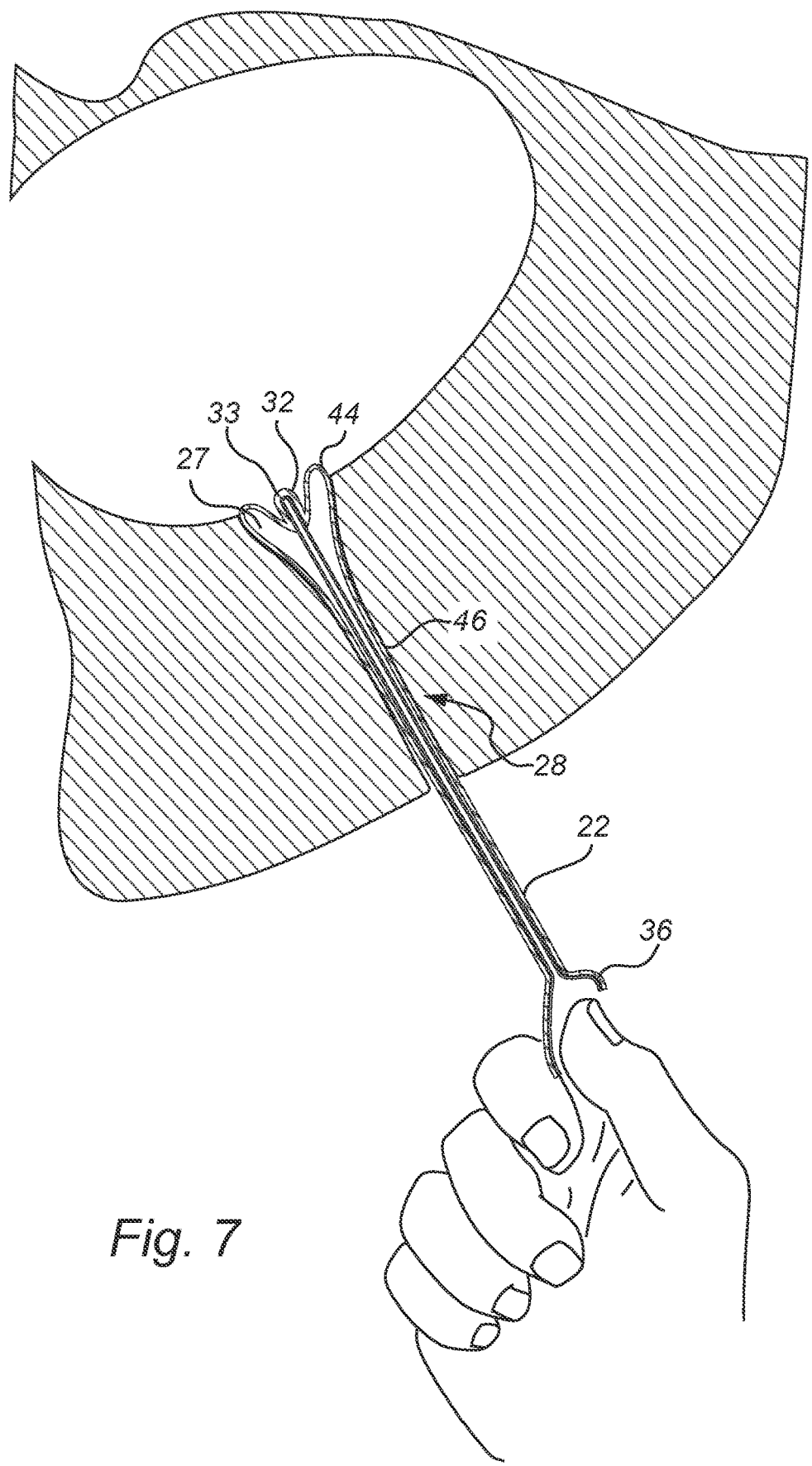
Figure 8:
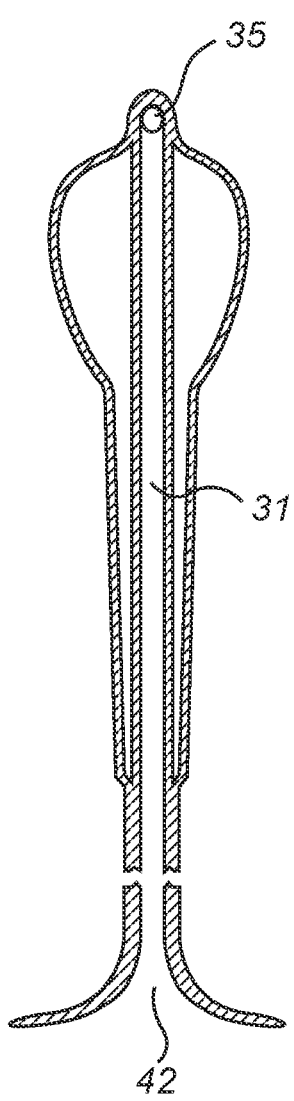
FIGS. 8, 9a and 9b are cross-sectional views of the catheter of embodiments of the present invention, illustrating various placement possibilities of the drainage openings.

The catheter shaft 22 includes an elongated hollow shaft, preferably with a single internal lumen, and with a tip region 32, terminating in a closed tip 33 that closes the catheter shaft 22 at its proximal end. At the distal end of the catheter shaft 22, the shaft terminates in a stopper member 36. The distal end has a discharge opening 42 (as best seen in FIG. 8 and forward), which is also preferably open to allow for ingress and egress of the removable stylet 28, to be accommodated by the hollow inner body of the shaft 22, and the internal lumen therein. The stylet 28 provides the apparatus 20 with stiffness for proper insertion into the urinary tract through the urethra 72 (FIGS. 5-7), with a portion of the catheter 20, in particular the tip 33 and the proximal portion of the overcoat layer 24, ultimately extending into the bladder neck 76 or bladder 78 (FIGS. 5-7).

For many applications, and where the catheter shaft 22 has a sufficient hardness and stiffness, the catheter can be inserted without the need for any stylet or similar insertion aids, simply by manipulating the catheter itself. Thus, for many applications, the stylet may be omitted. In particular, catheter shafts having a Shore A hardness of 70 or more may be used for such direct insertion, without any stylet or similar insertion aids.

The shaft 22 is preferably circular in cross-section. The inner diameter of the shaft 22 is preferably formed of a circular internal lumen that provides the shaft 22 with a hollow inner body. This hollow inner body is substantially uniform along its entire length, but may decrease at the tip region 32, as it closes in the tip 33. The outer diameter of the shaft 22 is preferably substantially uniform. However, the diameter in the tip region 32 may be greater than the remainder of the shaft 22 as this tip region 32 may be thickened with additional material layers placed onto the shaft 22. This outer diameter of the shaft 22, even at its largest in the tip region 32, is preferably less than the diameter of the undilated urethra. This added material at the tip region 32 provides the tip region 32 with additional rigidity for ease of insertion into the urethra 72 (FIGS. 5-7), and prevents the possibility of the stylet 28 from breaking through the tip 33.

The stopper member 36, attached to the shaft 22 at the proximal end of the shaft 22, forms a common opening 42 (as best seen in FIG. 8 and forward) with the shaft. This opening 42 also serves as the discharge opening, for draining urine out from the catheter. The stopper member 36 extends outward from the shaft 22. This stopper member 36 is preferably boat-like in shape, with its length and width being greater than the diameter of the shaft 22. This boat-like shape, coupled with these dimensions allows the stopper member 36 to be gripped and retained easily by the user as well as providing a barrier against over-insertion into the urethra.

Additionally, the boat-like shape allows the stopper member 36 to receive a correspondingly configured bar 60 on the stylet 28, that preferably abuts the inner surface of the stopper member 36, to serve to limit travel of the stylet 28 in the shaft 22, when the body member 21, with its tubular member 22 and overcoat layer 24, is elongated and deformed during insertion of the apparatus 20 into the urinary tract.

The shaft 22, including the tip region 32, and stopper member 36, that form the tubular member, are preferably an integral member, and form a single piece during the manufacturing process. However, multiple piece construction with fastening by conventional materials fastening techniques is also possible.

The shaft 22 is preferably made of an elastomeric material, that is also preferably medically acceptable, such as silicone rubber, and is preferably elastically deformable. A silicone rubber shaft 22 can be made by forming the tubular member 22 with uncured silicone rubber and then curing it. However, other suitable, medically acceptable polymeric materials may be used. These other suitable materials for manufacturing the shaft 22 include block copolymers (such as styrene-butadiene-styrene), urethanes and latex rubbers.

The overcoat layer 24 encircles the shaft 22 along a substantial portion of the length of the shaft 22. This overcoat layer 24 encases the fluid 27 in the cavity 26, such that it remains in the cavity 26 for the life of the catheter 20. The overcoat layer 24 preferably comprises a bulbous portion 44, proximally positioned on the shaft 22 and a sleeve portion 46, distally positioned on the shaft 22. The overcoat layer 24 is such that its cross-sectional diameter along at least a portion of either of its bulbous 44 and/or sleeve 46 portions, is at least equal to, and preferably greater than the diameter of the undilated urethra. The bulbous portion 44 is continuous with the sleeve portion 46. The sleeve portion 46 is preferably generally cylindrical and tapers outwardly, from rounded corners 48, to join the bulbous portion 44. The diameter of the bulbous portion 44 at its widest point is preferably greater than the diameter of the sleeve portion 46. However, the diameters of the bulbous portion 44 and the sleeve portions 46 could also be equal. The cavity 26, formed in the space between the overcoat layer 24 and the shaft 22, is preferably continuous, valveless and filled with a fluid 27, that remains encased therein.

The fluid 27 is preferably mineral oil but could also be a soft moldable semisolid such as petrolatum, petroleum jelly or a combination thereof. The fluid 27 could also be a gas, such as air or the like. The overcoat layer 24 is preferably an elastomeric material, such as silicone rubber, in order that it be elastically deformable such that the encased fluid 27 can flow from end to end therein when subject to pressure of the urethral walls that deform the overcoat layer 24 upon deployment in and removal from the urinary tract, while keeping the encased fluid from leaking from the cavity 26. The fluid 27 also serves to absorb shock from twisting or other movement of the shaft 22 when the catheter 20 is inserted in the urethra. The fluid 27 also allows the overcoat layer 24 to conform to the general shape of the urethra, and any irregularities in the urethra or other portions of the urinary tract.

The overcoat layer 24 is preferably of an elastomeric material that has a natural shape retaining memory. Coupled with the underlying fluid filled cavity 26, the overcoat layer 24 is gently reshaped during insertion and extraction by the pressure of the urinary tract, in particular that from the urethral walls 74 (FIGS. 5-7) and the bladder neck 76 (FIGS. 5-7). This gentle reshaping forces fluid from the bulbous portion 44 into the sleeve portion 46 during insertion of the catheter, whereby the diameter of the bulbous portion is greatly reduced, and the diameter of the sleeve portion slightly increased. The pressure exerted on the urethra is still minimal. When the bulbous portion enters into the bladder, there is no longer any compression force compacting the bulbous portion, and the bulbous portion retain its enlarged, relaxed shape, as fluid is transferred from the sleeve portion 46 to the bulbous portion 44. Upon extraction, fluid is again transferred from the bulbous portion 44 to the sleeve portion 46.

This gentle pressure engagement generally allows for the natural closure of the urethra 72 by forcing fluid 27 in the cavity 26 to the cavity portion within the bulbous portion 44 of the body member 21. Once in place, with the bulbous portion in the bladder, the pressure exerted on the urethra is very low, or even non-existent, and the closure is obtained by the bulbous portion resting on the bladder neck.

The overcoat layer 24 is preferably made of silicone rubber to be elastically deformable. However, other suitable materials such as block copolymers, e.g., styrene-butadiene-styrene, latex or other synthetic rubbers may also be used.

The stylet 28 is preferably a stiff, slightly flexible rod, that is removably inserted into the tubular member 22 through the opening 42 at the proximal end of the tubular member 22. The stylet 28 preferably has a body of a diameter slightly less than the inside diameter of the shaft 22 for easy insertion and withdrawal.

The body may have a round or blunt tip at its proximal end and an end member 56, at the distal end of the stylet 28. The end member 56 is preferably knob-like and shaped for a user's hand to comfortably press thereon to urge the stylet 28 into the shaft 22, and bear against the tip 33 of the tubular member 22. A bar 60, may be intermediate the tip 52 and end member 56, disposed preferably toward the distal end of the body in an orientation that is generally perpendicular to the axis of the body. The stylet 28 can e.g. be made of polycarbonate or other similar plastic to give the apparatus 20 the necessary rigidity to facilitate the insertion of the apparatus 20 into the urinary tract.

The length of the stylet 28 is preferably greater than the length of the shaft 22, such that when the stylet body is inserted all the way inside the shaft 22, with the distal end of the stylet 28 bearing against the tip 33, the end member of the stylet 28 is outside of the stopper member 36. Upon elongation and deformation of the body member 21, the bar 60 may be moved as far as into abutment with the stopper member 36, such that the stylet 28 is firmly within the hollow inner body of the tubular member 22 as the apparatus 20 is inserted into the urinary tract (shown in FIGS. 5-7 and described below).

Alternate embodiments of the apparatus 20, and in particular the body member 21, that operate nearly identical to the embodiment disclosed above, could be adapted for the male urinary tract, and in particular, for the urinary tract of a human male.

In order to enable drainage of urine through the catheter 20, the catheter also includes at least one drainage opening, eyelet 35, extending through the shaft 22, preferably at the tip region 32, to allow urine to enter the internal lumen of the shaft 22, to be discharged through the discharge opening 42 (as best seen in FIG. 8 and forward). Alternately, the stopper member 36 need not be present at all and the shaft 22 could be extended as long as desired, to function as a drainage tube.

In FIGS. 5-7, use and removal of the catheter from the urinary tract of a human female are illustrated. The catheter may be lubricated with water based lubricant, or other commonly used surgical lubricant. However, a coating providing low-friction to the surface may also be used.

Initially, the catheter 20, with the body member 21 in its relaxed, rest state (unelongated and undeformed) is placed into contact with the meatus 70 such that the distal tip region 32 enters the urethra 72. In this initial state, the overcoat layer 24, of the body member 21 with its bulbous 44 and sleeve 46 portions, is of a diameter equal to or greater than the diameter of the undilated urethra along at least a portion thereof. With the body member 21 in an unelongated state, the stylet 28, rests in the shaft 22 and tip region 32 of the tubular member 22, such that bar member 60 is approximately 1.5 cm from the stopper member 36. Then, as shown in FIG. 5 the initial insertion of the catheter 20 into the urethra follows, whereby the stopper member 36 prohibits further insertion of the body member 21. Additionally, the distal tip region 32 and part of the bulbous portion 44 extends at least into the bladder neck 76, and preferably with its distal tip 33 in the bladder 78.

With insertion complete, the stylet 28 has been removed, as shown in FIG. 6.

Pressure from the urethra walls 74, even when low or moderate, forces fluid 27 back into the bulbous portion 44, since no external forces act on the bulbous portion 44 once it has entered into the bladder. Thus, in the fully inserted position, the bulbous portion resumes its relaxed state, and with minimal pressure exerted on the urethra. However, in some embodiments, the urethral wall pressure may compress the overcoat layer 24 at the sleeve portion 46, such that the fluid volume in the bulbous portion 44, that has entered the bladder neck 76, or alternately, the bladder neck 76 and bladder 78, becomes greater than it was prior during insertion of the catheter 20, i.e. when the bulbous portion was within the urethra. Thus, when in the bladder, the diameter of the bulbous portion 44 may be greater than it was initially, prior to insertion, or of the same diameter as initially, prior to insertion. Thus, when inserted into the bladder, the bulbous portion generally reassumes its relaxed original form and shape.

With the stylet 28 removed, the body member 21 relaxes to its unelongated state, and is now properly seated in the female urinary tract. The entire overcoat layer 24 is now in the urinary tract, with the bulbous portion 44, and the tip region 32 of the shaft 22 extending into the bladder neck 76 or bladder 78, while the bulbous portion 44, and in particular the distal part of the bulbous portion, seats at the bladder neck 76, effectively blocking urine flow on the sides of the catheter, and effectively retaining the body member 21 in the urinary tract. The natural memory of the overcoat layer 24 coupled with underlying fluid filled cavity 26 serves to maintain a gentle pressure, exerted by the bulbous 44 and sleeve 46 portions within the urethra 72, on the urethral walls 74, in response to the pressure exerted by the urethral walls and the sphincter muscle. The resistance of this overcoat layer 24 is such that it conforms to the shape of the urethra 72, effectively sealing the urethra 72, apart from the internal lumen of the catheter, in addition to the bladder neck 76, thus blocking urine flow from the bladder on the outside of the catheter. This sealing by the body member 21 at the urethra 72 and bladder neck 76 serves to retain urine in the urinary tract until the catheter 20 is removed manually (as detailed below), or by voidance by opening of the valve (detailed above).

The retention element of the present invention, formed by the bulbous portion 44 and the sleeve portion 46, and the provision of a fluid in the cavity formed by these parts, is very advantageous. The transfer of fluid between the cavities enclosed by the bulbous portion 44 and the sleeve portion 46 occurs smoothly and continuously during insertion and removal of the catheter. This provides a certain resistance against the deformation, which is overcome by the manually exerted pushing and pulling force applied during insertion and removal of the catheter. At the same time, this resistance prevents that the catheter falls out involuntarily when inserted, even during temporarily increased pressure within the bladder, e.g. due to stress related incontinence. At the same time, an increased bladder pressure over a certain period of time, e.g. due to overfilling of the bladder, will transfer fluid from the bulbous portion 44 to the sleeve portion 46, and in the end automatically dispel the catheter from the urethra. This is of advantage, since it e.g. protects the kidneys.

When the catheter is to be removed, as shown in FIG. 7, the user 80 pulls on the stopper member 36 and the shaft 22

(including tip region 32) may be elongated, but this is in most cases not necessary, since the controlled deformation of the bulbous portion 44 and the sleeve portion 46 is normally sufficient to provide gentle insertion and removal of the catheter. The pulling force puts pressure on the overcoat layer 24 surrounding the bulbous portion 44, and forces fluid from the bulbous portion 44 into the sleeve portion 46, reducing the diameter of the bulbous portion 44. Hereby, fluid is moved from the bulbous portion, which hereby is reduced in diameter, and to the sleeve portion 46, which is then slightly enlarged. Upon continued outward pulling of the stopper member 36 by the user part of the sleeve portion 46 emerges from the meatus 70. The pressure from the urethral walls 74 and bladder neck 76, and in particular the sphincter muscle, forces fluid 27 to flow into the sleeve portion 46, that expands to accommodate this excess fluid 27. The outward pulling may also cause part of the bulbous portion 44 to extend beyond the distal tip 33, as the result of the pressure from the urethral walls 74 and the bladder neck 76, and in particular the sphincter muscle, that force fluid 27 into the sleeve portion 46.

The pulling continues until the catheter 20 has been completely removed from the urinary tract.

The overcoat layer and the retention element of the catheter can be produced in the way disclosed in WO 97/39697, said document hereby being incorporated in its entirety by reference.

The urinary catheter comprises a distal discharge opening 42, and one or several proximal drainage openings 35, connected through an internal lumen 31, as seen in FIGS. 1-4, 8 and 9.

The proximal drainage opening may be arranged in various ways, and at various positions. In one embodiment, as illustrated in FIG. 8, at least one proximal drainage opening 35 is arranged farther from the distal discharge opening 42 than the proximal end of the deformable fluid filled cavity, formed by the bulbous portion 44. Thus, the drainage opening 35 is here provided in a part of the catheter shaft extending beyond the overcoat layer.

In such embodiments, one or more drainage opening(s) 35 may be arranged in the side wall of the catheter shaft, as illustrated in FIG. 8, between the proximal end of the deformable fluid filled cavity and the proximal tip of the catheter shaft. Additionally, or alternatively, a drainage opening may also be provided at the tip, thereby forming a non-closed tip.

Figure 9B:
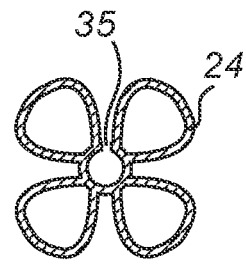
Figure 9A:
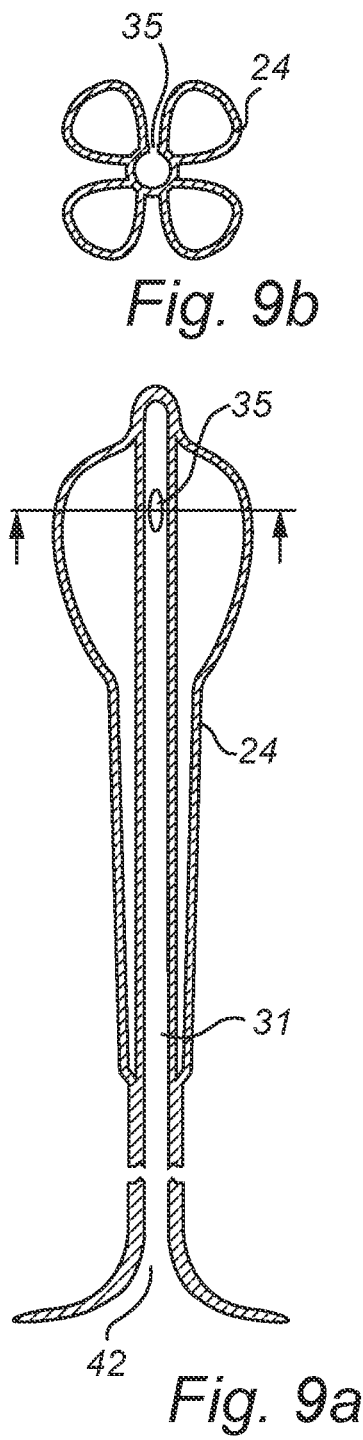

In another embodiment, illustrated in FIGS. 9a and 9b, the at least one proximal drainage opening 35 may be arranged at a part of the catheter shaft over which the overcoat layer 24 extends. To this end, a part of the deformable fluid filled cavity, formed by the overcoat layer 24, in the vicinity of the proximal end may have a non-circular cross-section, e.g. shaped as a four-leaf clover, forming indentations or vales in which one or more drainage openings may be provided. This is best seen in FIG. 9b. Many other cross-sectional shapes, apart from the four-leaf clover shape illustrated, are also feasible, clover shape with one, two or three petals, etc.

A valve 90 is provided to close the passage between the drainage opening(s) 35 and the discharge opening 42, through the internal lumen. The valve may be arranged at various positions, may be of various types and may be operated in various ways. Examples of such valves will be discussed in the following.

In some embodiment the valve is arranged to remain open when the valve actuator or handle is in a first state, and to remain closed when the valve handle or actuator is in a second state.

Figure 10A:
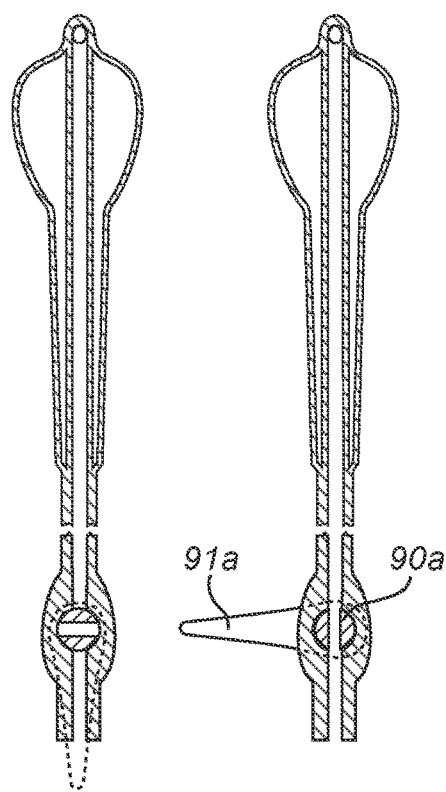
FIGS. 10a-18 are views at least partly in cross-section of catheters in accordance with embodiments of the present invention, illustrating different types of valves arranged in a distal, rearward part of the catheter.
Figure 10B:
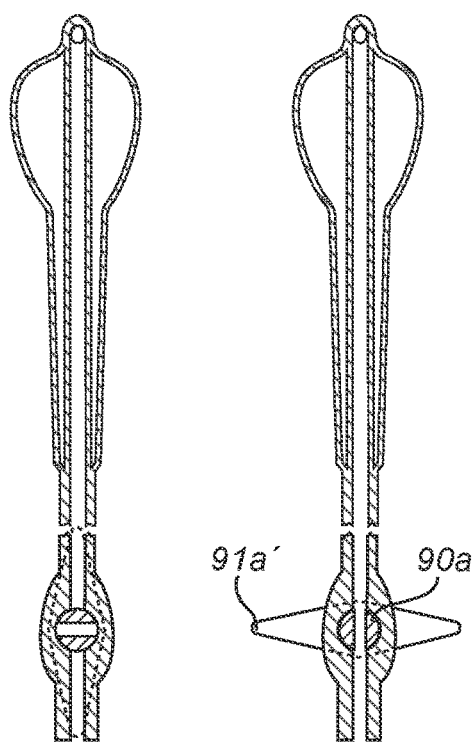

One such embodiment is illustrated in FIGS. 10a and 10b. The valve 90a is here a ball valve, which is a form of quarter-turn valve which may use a hollow, perforated and pivoting ball to control flow through it. It is open when the ball's hole is in line with the flow and closed when it is pivoted 90-degrees by the valve handle 91a. The ball need not be spherical, but may instead be e.g. cylindrical. The valve handle may extend as an arm towards only one side, as the handle 91a in FIG. 10a, or extend in two opposite directions, as the handle 91a' in FIG. 10b. In both FIGS. 10a and b, the left figure shows the valve in a closed state, whereas the right figure shows the valve in an open state. The valve and handle are here configured so that the handle is aligned with the longitudinal direction when closed, and extending laterally from the catheter when opened. However, alternatively, the valve and handle may be configured so that the handle is aligned with the longitudinal direction when opened, and extending laterally from the catheter when closed.

The valve is here arranged at or in the vicinity of the distal discharge opening. In particular, the valve can be arranged in a part of the catheter which is intended to remain outside the urethra in use. Preferably, the valve is arranged outside the stopper member, i.e. at a position farther from the proximal drainage opening than the stopper member.

Figure 11:
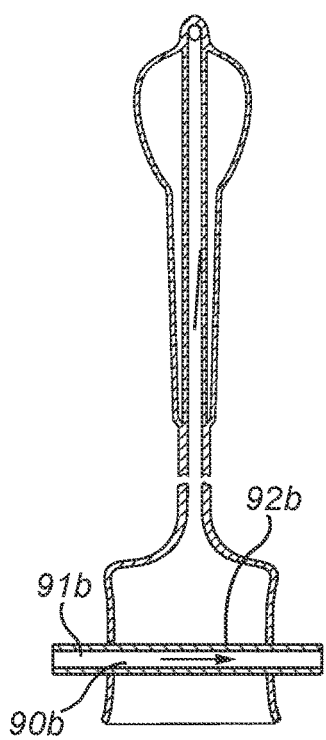

Another embodiment is illustrated in FIG. 11, in which the discharge end of the catheter comprises a flexible tube, and wherein the valve 90b comprises a handle in the form of a clamping or pinching element 91b. The handle may be formed as a jaw-like clamp, with two pivotable arms connected by a hinge, and with a lock fixing the pivotable arms together in the closed position. The handle may alternatively be a pinching element, having a gradually narrowing opening, which closes the tube by pinching when moved in the longitudinal direction of the element, as illustrated by the arrow 92b in FIG. 11.

In this valve arrangement, the valve is also arranged in the distal part of the catheter, in a part residing outside the urethra in use, and the valve is arranged to remain open once brought to the opened state.

Figure 12:
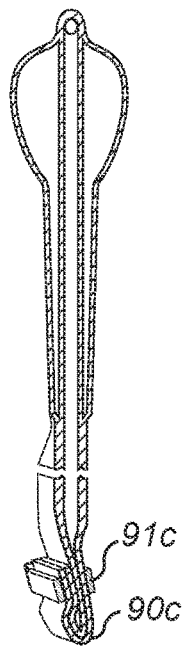

In another embodiment, illustrated in FIG. 12, the valve 90c comprises a foldable flexible tube, which may be folded to form a kink, thereby closing the valve. The tube may be maintained in the folded state by a handle, e.g. in the form of a clamp 91c as discussed in the foregoing embodiment.

In this valve arrangement, the valve is also arranged in the distal part of the catheter, in a part residing outside the urethra in use, and the valve is arranged to remain open once brought to the opened state.

Figure 13:
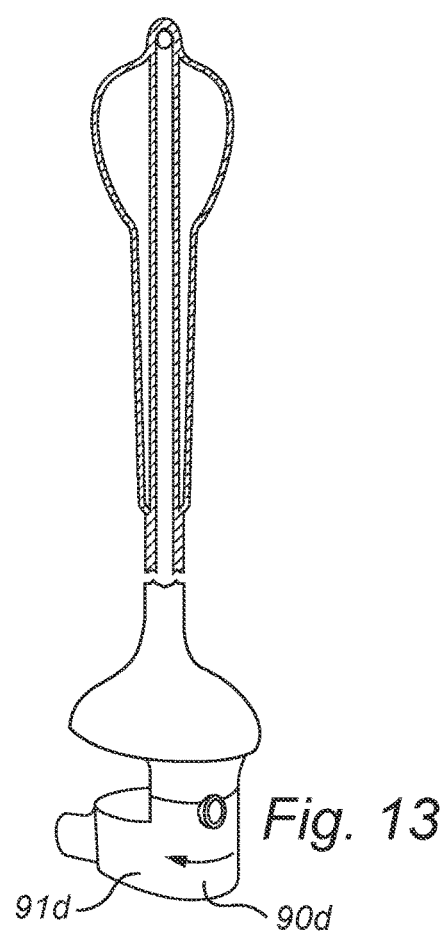

In another embodiment, illustrated in FIG. 13, the valve 90d comprises a rotatable part, which is rotatable around the longitudinal axis of the catheter. The rotatable part may comprise a part of the internal lumen, which is arranged off-center, whereby this part of the internal lumen is aligned with the remainder of the internal lumen in one rotational position, whereby the valve is in an open state, and to be displaced in relation to the remained of the internal lumen in another rotational position, whereby the valve is in a closed state. The rotatable part may comprise a gripping surface, a protruding part, or the like, to serve as a handle 91d for manually rotating the rotatable part. Preferably, the handle and valve are configured so that the handle is relatively small, and so that the handle extends in a direction not directed towards the user's legs when closed, to make it more comfortable.

In this valve arrangement, the valve is also arranged in the distal part of the catheter, in a part residing outside the urethra in use, and the valve is arranged to remain open once brought to the opened state.

Figure 14:
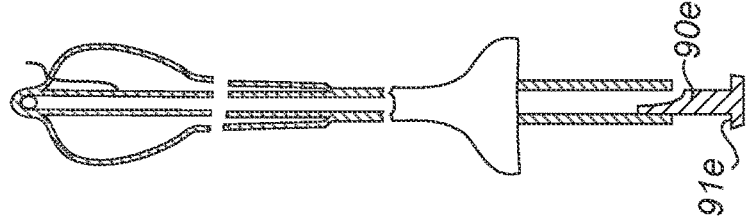
Figure 14:
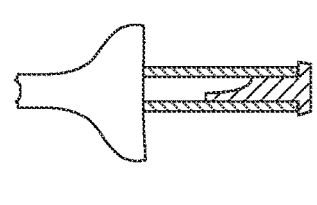

In another embodiment, as illustrated in FIG. 14, the valve 90e is arranged in the distal end of the catheter. The valve is here in the form of a moveable tip, arranged within the end of the internal lumen. The tip comprises a lumen, extending from a proximal opening to a distal opening, arranged in the sidewall of the tip. When arranged in a fully inserted position, the distal opening is closed by the side walls of the internal lumen, and when brought to a displaced, extracted position, the distal opening is exposed, wherein the valve is opened. This type of valve generally resembles the valve type used in sport bottles. The valve may be provided with an extended flange, or other gripping structure, to function as a handle 91e for the valve. The top left figures of FIG. 14 illustrate the valve in an open state, seen from two different rotational positions, whereas the two bottom figures show the valve in a closed state, seen in the same two different rotational positions.

In this valve arrangement, the valve is also arranged in the distal part of the catheter, in a part residing outside the urethra in use, and the valve is arranged to remain open once brought to the opened state.

Figure 15:
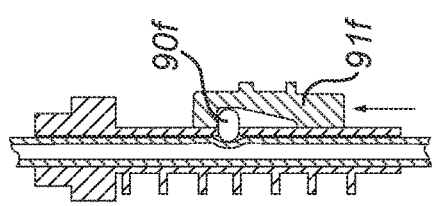
Figure 15:
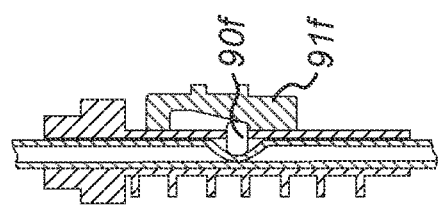

In another embodiment, as illustrated in FIG. 15, the catheter also comprises a flexible tube arranged in a distal part of the catheter. The pinch valve 90f here comprises a laterally displaceable part, which is in contact with the flexible tube, and which is arranged to be moved towards the flexible tube, thereby closing it, as shown in the lower figure of FIG. 15, when a slidable handle 91f is slid to a first position, e.g. an upper position, and be allowed to moved away from the tube, thereby opening the valve, as shown in the upper figure of FIG. 15, when the handle 91f is slid to a second position, e.g. a lower position.

In this valve arrangement, the valve is also arranged in the distal part of the catheter, in a part residing outside the urethra in use, and the valve is arranged to remain open once brought to the opened state.

Figure 17:
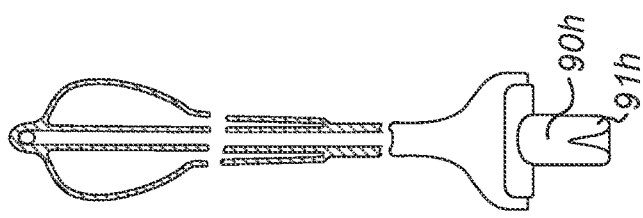
Figure 16:
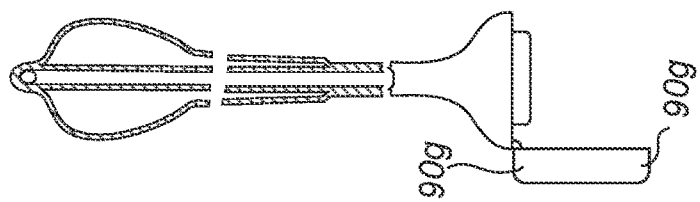
Figure 16:
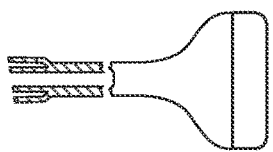

In another embodiment, as illustrated in FIG. 16, the valve 90g is formed by a lid, closing off the drainage opening in the closed state. The lid is manually openable, and is provided with a gripping surface, a gripping tab, or other form of handle 91g. The lid is preferably connected to the catheter by a hinge, so that it remains connected to the catheter also in the open state. However, a completely removable lid may also be used. In FIG. 17, a similar valve 90h is shown, where the drainage opening is closed by a plug. The plug may be arranged to remain in place, in the closed state, by friction. To enhance friction, it may also be provided with a corrugated surface, flanges and the like. However, the plug may also comprise external threading, corresponding to internal threading in the drainage opening, to be screwed into place. Alternatively, the plug and catheter interface may also comprise a bayonet connection or the like. The plug is also provided with a gripping surface or similar type of handle 91h, and is removable from the drainage opening for opening of the valve, and insertable into the opening for closing the valve.

In this valve arrangement, the valve is also arranged in the distal part of the catheter, in a part residing outside the urethra in use, and the valve is arranged to remain open once brought to the opened state.

Figure 18:
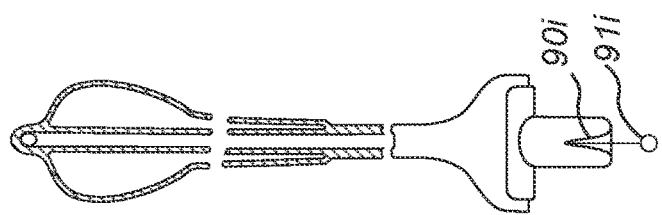
Figure 18:
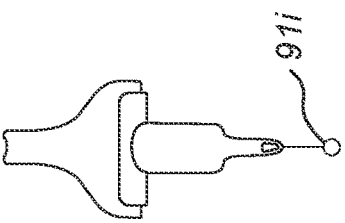

In another embodiment, illustrated in FIG. 18, the valve 90i comprises a flexible tube end with an opening, which in the closed state is folded and inverted inwardly into the drainage opening, whereby the opening is compressed and closed. A handle 91i, e.g. in the form of a string with an optional gripping ring, or a rod, may be used to pull out the flexible tube end from the discharge opening, thereby opening the valve. For closing the valve, the flexible tube end can again be inverted into the drainage opening.

In this valve arrangement, the valve is also arranged in the distal part of the catheter, in a part residing outside the urethra in use, and the valve is arranged to remain open once brought to the opened state.

In some embodiments the valve is arranged to be open only when the valve is continuously activated and manipulated, by an actuator or handle, and to resume the closed state as soon as the valve handle or actuator ceases its activation on the valve. Some such embodiments will now be discussed.

Figure 20:
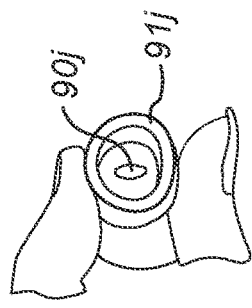
FIGS. 19-21 are perspective views of catheters in accordance with further embodiments of the present invention, illustrating different types of valves arranged in a distal, rearward part of the catheter.
Figure 20:
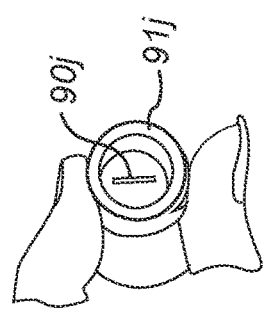
Figure 19:
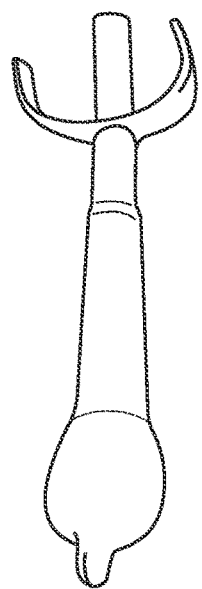

In one such embodiment, illustrated in FIGS. 19 and 20, the catheter comprises valve 90j in the form of a duckbill valve arranged at, or in the vicinity of, the drainage opening. The duck bill valve generally act as backflow prevention valve, and has elastomeric lips in the shape of a duckbill which extend into the drainage open and/or the internal lumen. A handle 91j, e.g. in the form of a rim encircling the duckbill valve, may be used to manipulate the valve. By compressing the handle, and thereby the valve, in a direction along the width of the duckbill, the duckbill lips are moved apart, thereby opening the valve, as illustrated in FIG. 20. As soon as the compression ceases, the lips return to their closed position, thereby again closing the valve.

In FIG. 20, the duckbill valve is arranged so that the opening extends generally perpendicularly to the longitudinal direction of the stopper member. However, the opening may also be arranged in other directions, such as extending generally in the same direction as the longitudinal direction of the stopper member. Such an arrangement is generally preferred, since it reduces the risk of the valve unintentionally opening as the user moves.

The valve 90j and handle 91j are preferably arranged outside the stopper member, i.e. in a position farther from the proximal drainage opening than the stopper member. In the illustrated embodiment, the handle and valve are arranged relatively close to the stopper member, but may alternatively be arranged farther away from the stopper member, to allow easier access.

Figure 21:
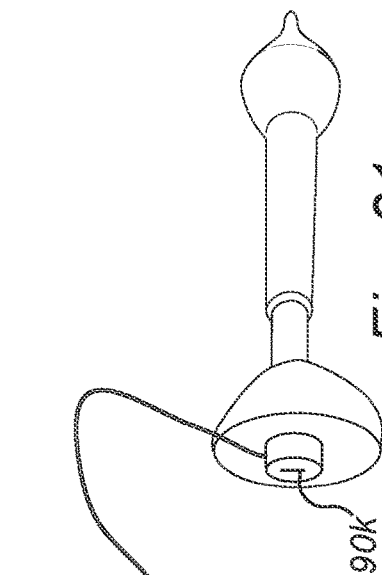
Figure 21:
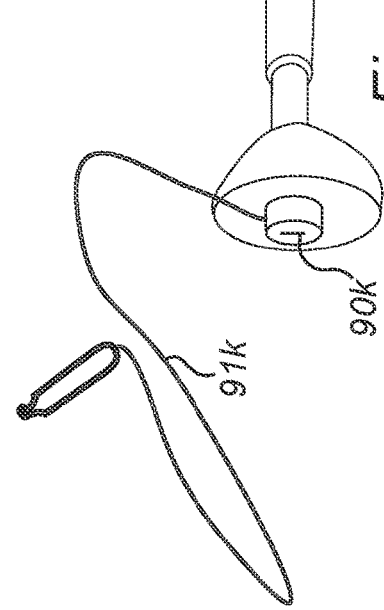

Alternatively, the compression of the valve can be arranged from a more remote position, e.g. by providing strings connected to the rim around the valve, whereby pulling of the strings provides a force across the width of the duckbill lips, thereby opening the valve. Such an embodiment is illustrated in FIG. 21, where the handle 90k, in the form of strings, are arranged to remotely control the duckbill valve 90k.

In these valve arrangements, the valve is also arranged in the distal part of the catheter, in a part residing outside the urethra in use, but the valve is arranged to be open only upon continued manipulation of the valve.

Figure 22:
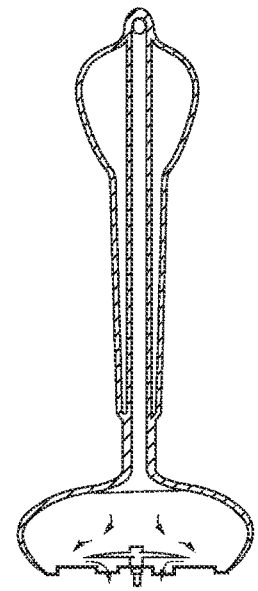
Figure 22:
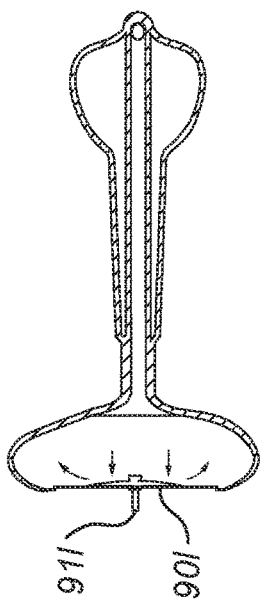

In another embodiment, illustrated in FIG. 22, the valve 90l is an umbrella valve, comprising a diaphragm shaped or umbrella shaped sealing disc. The disc overlays an outlet opening, and prevents flow out from the catheter when not actively lifted, but allows flow in the same direction when the disc is lifted up from the opening. The disc may preferably be convex. The disc can be controlled by a handle 91l, e.g. in the form of a rod connected to the center of the disc. By pushing the rod in the direction towards the tip of the catheter, the disc is lifted, and the valve is opened to discharge urine. As soon as the pushing ceases, the disc will immediately, due to the force of the urine and gravity, resume its closed state. However, the valve may also be actively pulled into a closed state by manipulation of the handle. In the figure to the left, the valve is illustrated in its closed state, and in the figure to the right in its open state.

In this valve arrangement, the valve is also arranged in the distal part of the catheter, in a part residing outside the urethra in use, but the valve is arranged to be open only upon continued manipulation of the valve.

In another embodiment, illustrated in FIG. 23, the valve 90$m$ is again of a duckbill type, but with a different type of handle. Here, the handle 91$m$ is in the form of relatively rigid tabs extending in opposite direction away from the valve. The tabs, when compressed, exerts a force to pull the lips of the duckbill valve apart, thereby opening the valve. In this arrangement, the force exerted on the valve is a pulling force rather than a pushing force, and consequently the force may be applied in orthogonal direction to the width direction of the duckbill. The figure to the left illustrates the valve in a closed state, with no compression force applied, and the figure to the right illustrate the valve in an open state, with a compression force applied.

In FIG. 23, the duckbill valve is arranged so that the opening extends generally in the longitudinal direction of the stopper member. Such an arrangement is generally preferred, since it reduces the risk of the valve unintentionally opening as the user moves. However, the opening may also be arranged in other directions, such as extending generally perpendicularly to the longitudinal direction of the stopper member.

The valve 90$m$ and handle 91$m$ are preferably arranged outside the stopper member, i.e. in a position farther from the proximal drainage opening than the stopper member. In the illustrated embodiment, the handle and valve are arranged relatively close to the stopper member, but may alternatively be arranged farther away from the stopper member, to allow easier access.

In the illustrated example of FIG. 23, the handle is arranged to open the valve by pushing the handle parts together. To this, the handle parts are preferably in the form of relatively rigid tabs, enabling transfer of a force to the attached ends by pushing the loose ends together. Thus, in this embodiment, the handle parts functions as lever arms.

Figure 37:
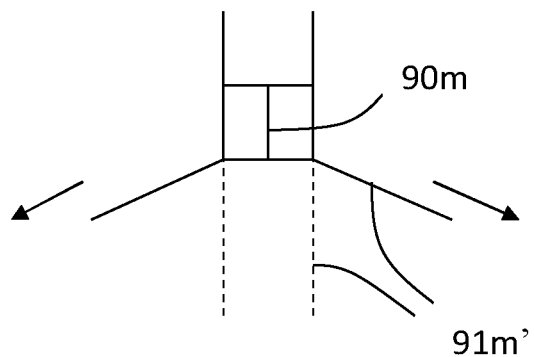
FIGS. 37 and 38 are schematic, cross-sectional illustration of further embodiments of valves with handling parts, in accordance with embodiments of the present invention.

However, the same handle arrangement may also be used to open the valve by pulling the handle parts away from each other, such as illustrated in FIG. 37. In such a realization, the handle parts 91$m$' may be made of a more flexible material, which is generally easier and more cost-efficient to produce. This also minimizes the risk of the user coming in contact with the discharge urine, since the fingers used for manipulation will be pulled away from the valve during discharge. Here, the handle parts 91$m$' may be in the form of tabs, arranged on opposite sides of the duckbill valve. The tabs may be arranged to extend essentially distally, i.e. in the axial direction of the catheter shaft, when not in use, as illustrated with dashed lines in FIG. 37. The user may then separate the tabs and pull them apart for opening of the valve, when urine is to be discharged, as illustrated by solid lines in FIG. 37. In this embodiment, the tabs may to some extend stick together when not in use, thereby providing an additional closure of the valve. The tabs may be provided as narrow tabs, having a width essentially corresponding to the width of the duckbill valve, or even smaller. However, tabs with greater widths may also be used, such as tabs having essentially the same width as the enlarged rearward part of the catheter. In such embodiments, the tabs may have a width exceeding, or even greatly exceeding the width of the duckbill valve, such as having a width being 2-3 times the width of the duckbill valve.

The handles, e.g. in the form of tabs, arranged to open the duckbill valve by pulling the handles/tabs apart may still be operated by only one hand, e.g. by gripping one of the handles/tabs between the thumb and another finger, and the other handle/tab between two other fingers.

Figure 38:
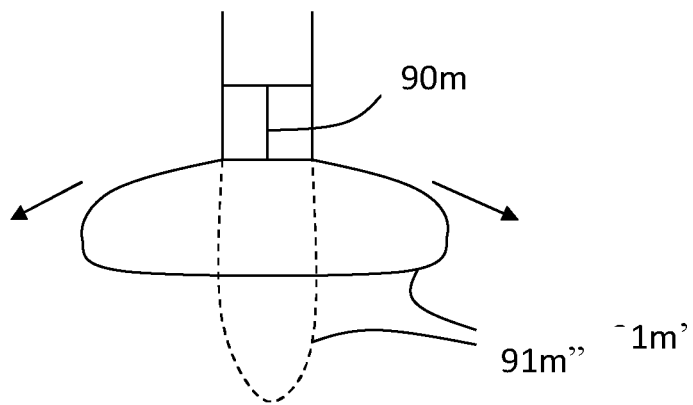

As illustrated in FIG. 38, the handles/tabs 91$m$" may also be connected at their distal ends, thereby forming a loop. In such an embodiment manipulation with only one hand can be made even simpler, e.g. by inserting two fingers into the loop and moving them apart. In this embodiment, the loop will protrude primarily distally, in the axial direction of the catheter shaft, when not in use, as illustrated with dashed lines in FIG. 38. The user may then e.g. insert two fingers into the loop and separate them to extend the loop in a transversal direction, as illustrated in solid lines in FIG. 38, thereby pulling the tabs apart for opening of the valve, when urine is to be discharged.

In this valve arrangement, the valve is also arranged in the distal part of the catheter, in a part residing outside the urethra in use, but the valve is arranged to be open only upon continued manipulation of the valve.

In another embodiment, as illustrated in FIGS. 24 and 25, the valve is controllable by an actuator. Here, the valves 90$n$ and 900 comprise a valve member of ferromagnetic material, such as iron, biased to be in a closed position if inactivated. By activation of an actuator, 91$n$ and 91$o$, for example in the form of a magnet, the valve member is displaced to an opened position, bringing the valve to an open state. This activation can be achieved from a remote position, without physical contact. The figures to the left illustrate the valves in a closed state, whereas the figures to the right illustrate the valves in an open state. The valve element may e.g. be in the form of a ball, as illustrated in FIG. 24, or in the form of a plate, hingedly connected to the catheter, as illustrated in FIG. 25.

In this valve arrangement, the valve is also arranged in the distal part of the catheter, in a part residing outside the urethra in use, but the valve is arranged to be open only upon continued manipulation of the valve.

Figure 26:
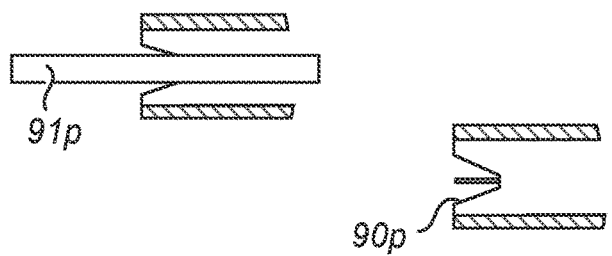
Figure 26:
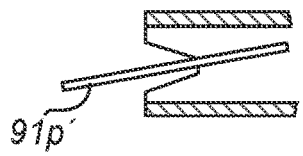
Figure 27:
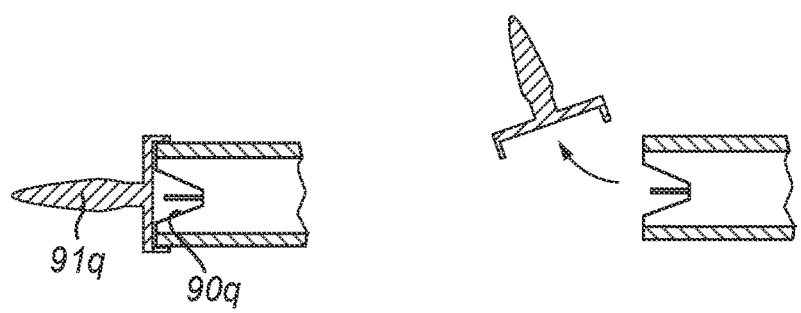
Figure 28:
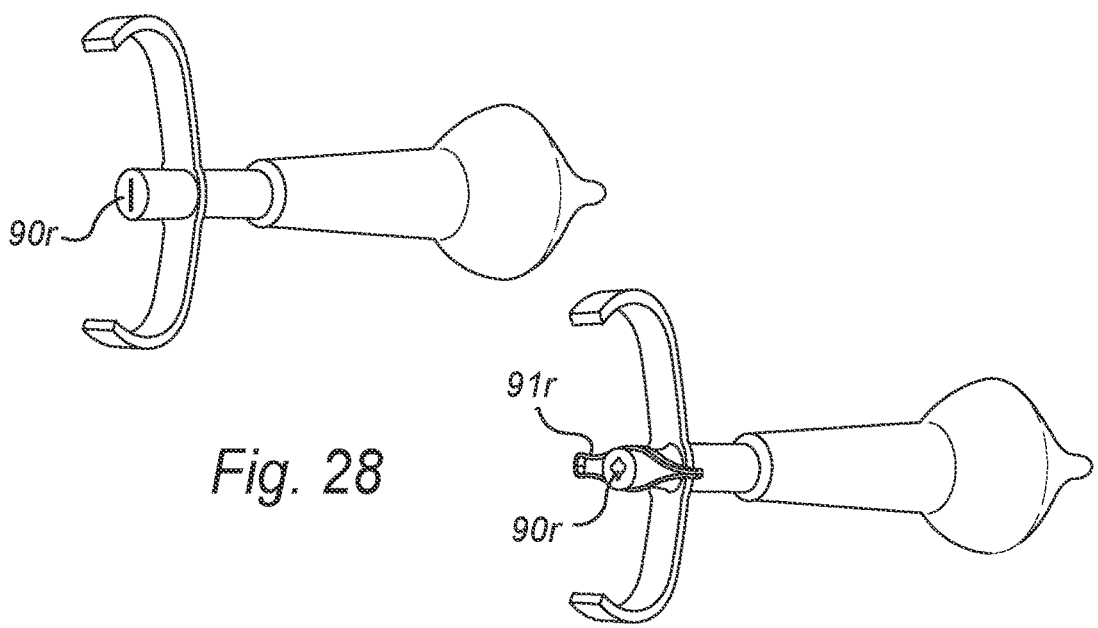

In other embodiments, illustrated in FIGS. 26-28, the valves comprise other types of mechanical activators. In the embodiment of FIG. 26, the valve is a duckbill valve, of the same or similar type as discussed in previously discussed embodiments. Here, an actuator 91$p$ for opening of the valve may be hollow, e.g. in the form of a tube. For opening of the valve, the tube is inserted through the lips, allowing urine to pass inside the lumen of the tube. Alternatively, the actuator 91$p$' could be solid, e.g. in the form of a rod or the like. For opening of the valve, the rod is inserted into the valve, through the lips, allowing urine to pass at the sides of the rod.

A similar type of valve is illustrated in FIG. 27. Here, the valve 90$q$ is also a duckbill valve. The actuator 91$q$ is in the form of a lid, with an outwardly protruding extension, e.g. in the form of a pin, post or the like. The lid may be arranged over the outlet opening of the valve, and when the valve is to be opened, the lid may be removed from the valve, and the protruding extension be used in the same way as the rod in the previously discussed embodiment, for insertion into the valve, to separate the duckbill lips apart.

In the embodiment of FIG. 28, the valve 90$r$ is of the type which is opened by compression of two opposite sides of the valve, such as a duckbill valve, and the same or similar as the embodiments discussed in relation to FIGS. 19 and 20.

Here, however, the compression force is applied with an actuator 91r, e.g. in the form of a pair of tweezers, pinchers, a forceps, tongs, or the like. This allow the compression force to be applied more easily, and also from a certain distance from the discharge opening and the outflowing urine.

In these valve arrangements, the valve is also arranged in the distal part of the catheter, in a part residing outside the urethra in use, and the valve is arranged to be open only upon continued manipulation of the valve.

In the embodiments discussed so far, the valve is arranged in the distal part of the catheter, in a part residing outside the urethra in use. However, it is also feasible to arrange the valve in other positions, such as at or close to the proximal tip, or in intermediate positions, between the distal discharge opening and the proximal drainage opening. In the following, some embodiments in which the valve is arranged at, or in the vicinity of, the proximal tip will be disclosed in further detail.

Figure 29:
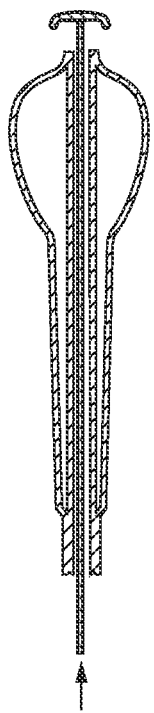
FIGS. 29-33 are cross-sectional views of catheters in accordance with embodiments of the present invention, illustrating different types of valves arranged in a proximal part of the catheter.

In the embodiment illustrated in FIG. 29, the valve 90s is arranged in the upper, proximal part of the catheter. Here, the valve is in the form of an umbrella valve, with a disc or membrane which extends over a central proximal opening of the catheter. A handle 91s, such as a rod attached to the disc/membrane, and extending through the internal lumen, and extending beyond the proximal drainage opening, can be manipulated from the distal side of the catheter to lift the disc/membrane over the drainage opening, thereby opening the valve. When not manipulated, the pressure exerted by the urine in the bladder closes the valve, thereby prohibiting drainage of urine through the catheter.

In this valve arrangements, the valve is arranged in the proximal part of the catheter, in a part residing inside the bladder in use, and the valve is arranged to be open only upon continued manipulation of the valve.

Figure 30:
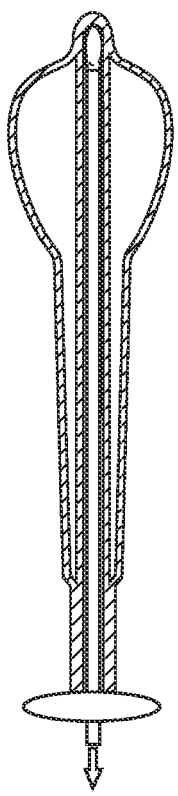

In another embodiment, as illustrated in FIG. 30, the valve 90t is formed by an insertable part, connected to a handle 91t, which in a first, fully inserted position blocks the drainage opening of the catheter, and which in a retracted position opens the drainage opening for drainage. To this end, the handle may e.g. comprise a tube with a central opening, whereby the sidewalls of the tube closes the drainage opening when inserted into the lumen, Thus, by pulling the handle downwards, in a distal direction, the valve is brought to its open state, whereas pushing the handle back brings the valve to its closed state.

In this valve arrangements, the valve is arranged in the proximal part of the catheter, in a part residing inside the bladder in use, and the valve is arranged to remain open when once brought to the open state, and to be brought back to a closed state upon further manipulation of the valve.

Figure 31:
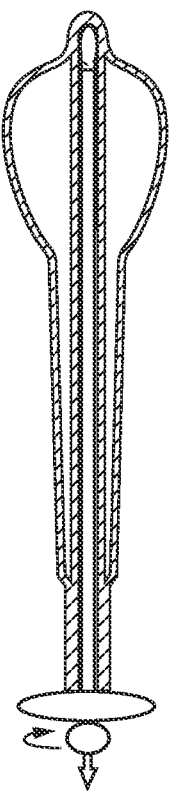

In another embodiment, as illustrated in FIG. 31, the valve 90v is formed by an insertable part, connected to a handle 91v. In this embodiment, the handle may be formed as a tube, with an opening arranged through a sidewall in the proximal part. In a first rotational position, this opening is aligned with a drainage opening of the catheter, thereby forming an open state for the valve. In another rotational position, the opening of the handle is not aligned with the drainage opening, thereby closing the opening, whereby the valve is in a closed state. Thus, by rotating a distal part of the handle, preferably extending beyond the distal end of the catheter, the valve can be brought to an open or closed state.

In this valve arrangements, the valve is arranged in the proximal part of the catheter, in a part residing inside the bladder in use, and the valve is arranged to remain open when once brought to the open state, and to be brought back to a closed state upon further manipulation of the valve.

Figure 32:
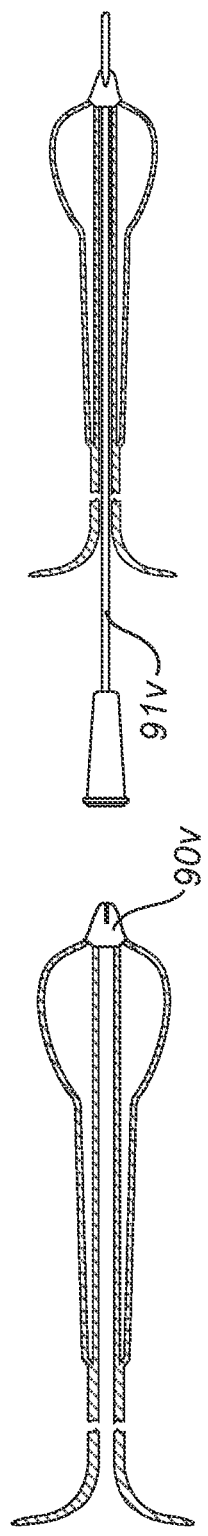

In another embodiment, illustrated in FIG. 32, the valve 90v is in the form of a duckbill valve, arranged at the proximal tip of the catheter. Similar to the embodiment discussed in relation to FIG. 26, the valve can be opened by a handle 91v, e.g. in the form of a tube or a rod. For opening of the valve, the rod/tube is inserted into the internal lumen of the catheter, through the discharge opening, and moved to a position in which the upper part of the rod or tube extends beyond the proximal tip of the catheter, and through the valve 90v.

In this valve arrangements, the valve is also arranged in the proximal part of the catheter, in a part residing inside the bladder in use, and the valve is arranged to be open only during continuous activation by the handle, to resume its closed state once the handle activation ceases.

Figure 33:
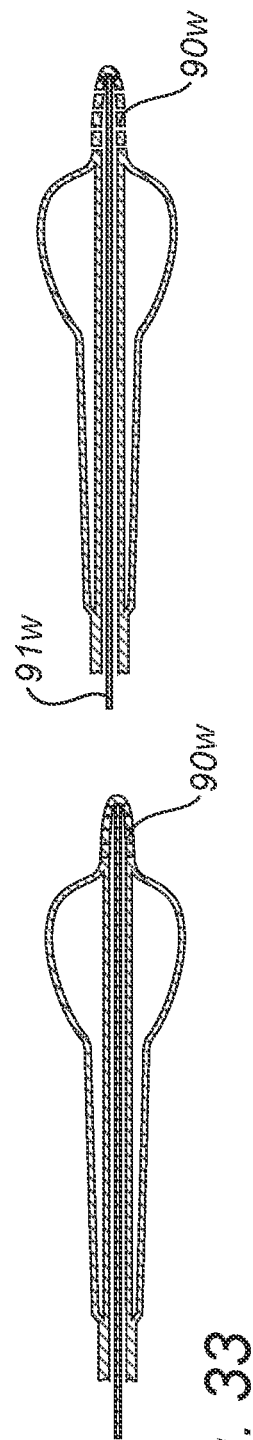

In yet another embodiment, illustrated in FIG. 33, the valve 90w is in the form of an expandable tip, arranged as the proximal tip of the catheter. The expandable tip can be expanded into an expanded state, in which perforations or openings in the tip wall opens up, allowing drainage of urine through the tip wall. In a contracted state, the perforations or openings are closed. A handle 91w, such as a rod, can be used to activate the valve, by pushing the end of the tip upwards, in a proximal direction, thereby causing the tip to be expanded.

In this valve arrangements, the valve is also arranged in the proximal part of the catheter, in a part residing inside the bladder in use, and the valve is arranged to be open only during continuous activation by the handle, to resume its closed state once the handle activation ceases.

In the embodiments discussed above in which a rod is used as a handle for manipulating the valve, the stylet used for insertion of the catheter into the urethra may be used also as the handle for manipulating the valve. However, alternatively, a separate rod may be used to this end.

Further, as mentioned in the foregoing, an insertion aid is in many realizations of the urinary catheter not necessary, since the catheter shaft in itself is stiff and hard enough to enable insertion and extraction of the catheter into the urethra, without the need for any additional insertion aid.

In case an insertion aid should be used, there are various ways to provide adequate interaction between the insertion aid, such as a stylet, and the catheter. As discussed in the foregoing, in relation to FIGS. 8-9, the proximal drainage opening(s) can be arranged on a sidewall of the catheter, and/or centrally on the tip end. If the drainage opening(s) are only arranged on the sidewall, the tip end may be closed, forming a closed tip, which is of advantage, since the closed tip can then be engaged by the stylet during insertion of the catheter into the urethra, in the way discussed in relation to FIGS. 5-6. However, the stylet can be used in a similar way also for catheters with an opening arranged centrally at the tip end, i.e. for catheter with a non-closed tip. Some exemplary embodiments will be discussed in the following.

Figure 34:
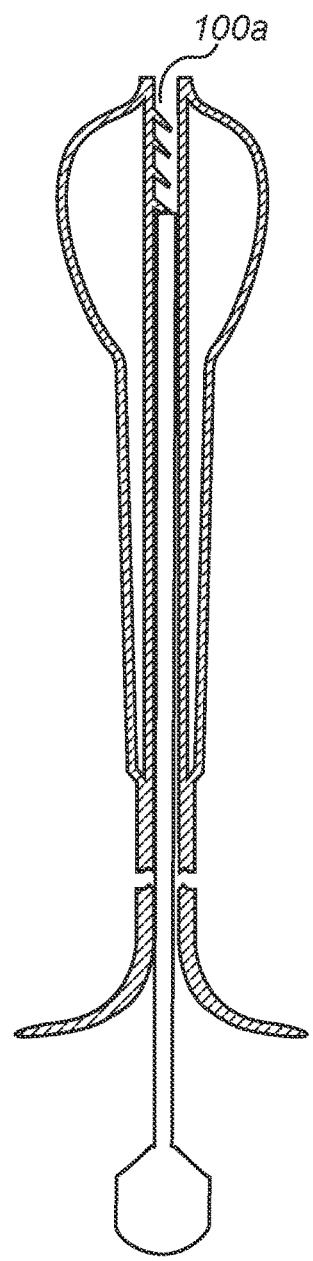
FIGS. 34-36 are cross-sectional view of catheters in accordance with embodiments of the present invention, illustrating different interaction between the catheter and an insertion aid.

In a first such embodiment, illustrated in FIG. 34, engagement elements 100a are arranged inside the internal lumen of the catheter. The engagement elements are preferably arranged relatively close to the proximal tip of the catheter, and are preferably dimensioned so that the flow capacity of the internal lumen remains essentially the same as without the engagement elements. The engagement elements may e.g. be in the form of one or several barbs. When a stylet is inserted into the internal lumen, the engagement elements will engage with the stylet once the stylet end reaches them, thereby hindering further insertion, and thereafter transfer-ring the force of the stylet to the catheter. In this embodiment, the stylet preferably has an outer dimension which is only slightly smaller than the internal diameter of the internal lumen. However, additionally or alternatively, the stylet may also comprise additional engagement elements, such as barbs, flanges or the like, to engage with the catheter.

Figure 35:
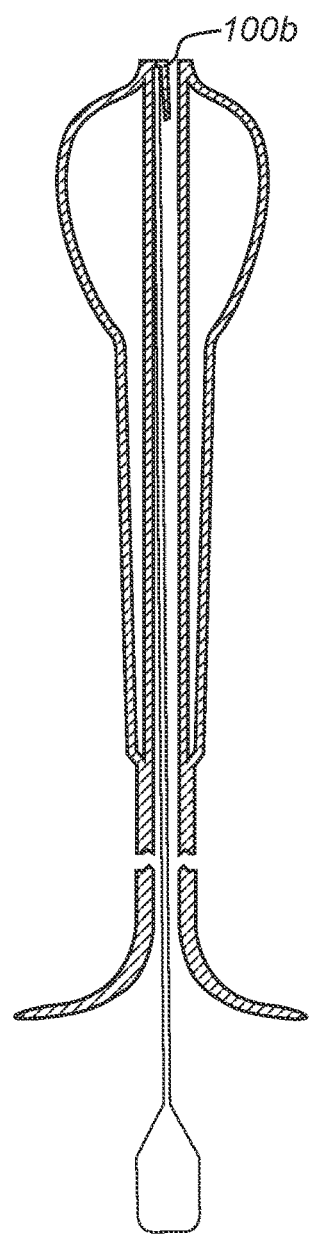

In a second embodiment, illustrated in FIG. 35, the engagement element 100b is instead arranged as a pocket arranged at or in the vicinity of the proximal tip of the catheter. When the stylet is inserted into the internal lumen of the catheter, it may be guided so that the proximal end of the stylet enters into the pocket, whereby the force of the stylet can be 0 transferred to the catheter. In this embodiment, the stylet can have an outer diameter which is smaller, and possibly even much smaller, than the internal diameter of the internal lumen.

Figure 36:
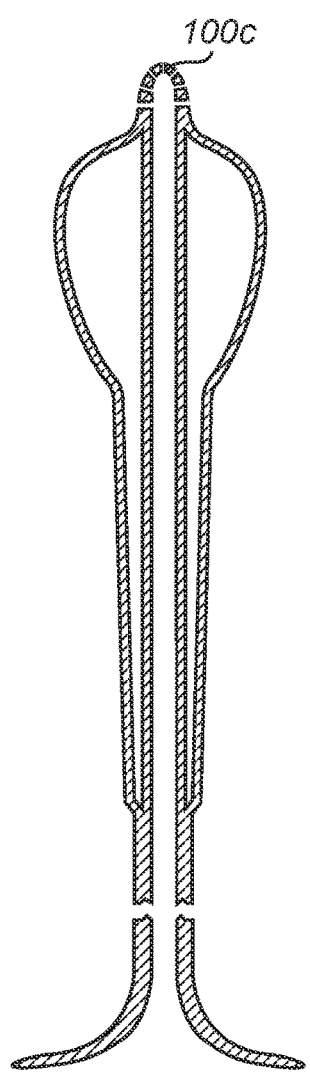

In a third embodiment, illustrated in FIG. 36, the proximal tip of the catheter can be semi-closed. The semi-closed tip may then function as an engagement element 100c. The semi-closed tip has one or more small openings, which are large enough to allow urine to be drained through them, but small enough to prevent the stylet to pass through them. Thus, in this embodiment, the outer diameter of the stylet is greater, and preferably significantly greater, than the internal diameter of the openings in the tip. Thus, the tip will hereby engage with the stylet, and allow the force of the stylet to be transferred to the catheter.

Specific embodiments of the invention have now been described. However, several alternatives are possible, as would be apparent for someone skilled in the art. For example, features from the above-discussed embodiments may be combined in various ways.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A urinary catheter for insertion into the urethra comprising:
   a catheter shaft with an outer surface and an internal lumen, extending between a distal discharge opening and at least one proximal drainage opening, arranged at or in the vicinity of a proximal tip of the catheter shaft;
   an overcoat layer encircling at least a portion of said catheter shaft and extending substantially along said catheter shaft, thereby forming a closed deformable fluid filled cavity intermediate said overcoat layer and said outer surface, said fluid filled cavity having a proximal end and a distal end, wherein said overcoat layer is elastically deformable to allow for movement of said fluid within said cavity during deployment, wherein the fluid filled cavity is arranged to deform upon insertion of said catheter shaft into the urethra, whereby at least a portion of said fluid filled cavity at said proximal end is arranged to be compressed to a smaller diameter, and upon continued insertion of said catheter shaft through the urethra into at least the bladder neck, at least said portion of said fluid filled cavity at said proximal end being arranged to expand back toward a greater diameter, as the fluid of said fluid filled cavity at said distal end is caused to flow toward the proximal end of the fluid filled cavity;
   a valve arranged to set the internal lumen of the catheter shaft in an open or closed state; and
   a valve handle or actuator arranged to bring the valve to an opened state upon activation, wherein the valve is a duckbill valve and wherein the valve handle comprises tabs extending from the duckbill valve on opposite sides thereof.

2. The urinary catheter of claim 1, wherein said at least one proximal drainage opening is arranged farther from said distal discharge opening than said proximal end of the deformable fluid filled cavity.

3. The urinary catheter of claim 1, wherein said at least one proximal drainage opening is arranged at a part of said catheter shaft over which said overcoat layer extends.

4. The urinary catheter of claim 1, wherein the valve is arranged to remain closed as a default, and to be opened only when the valve handle or actuator is continuously activated, and to resume its closed state when activation of the valve handle or actuator ceases.

5. The urinary catheter of claim 1, wherein the valve is arranged at or in the vicinity of the distal discharge opening.

6. The urinary catheter of claim 1, wherein the catheter shaft has a Shore A hardness in the range of 75-85.

7. The urinary catheter of claim 1, wherein the valve is controllable with a handle, which is non-removably connected to the valve.

8. The urinary catheter of claim 1, wherein the catheter shaft comprises a closed proximal tip.

9. The urinary catheter of claim 1, wherein the tabs are connected at their distal ends, thereby forming a loop.

10. A urinary catheter for insertion into the urethra, comprising:
    a catheter shaft with an outer surface and an internal lumen, extending between a distal discharge opening and at least one proximal drainage opening, arranged at or in a vicinity of a proximal tip of the catheter shaft;
    an overcoat layer encircling at least a portion of said catheter shaft and extending substantially along said catheter shaft, thereby forming a closed deformable fluid filled cavity intermediate said overcoat layer and said outer surface, said fluid filled cavity having a proximal end and a distal end, wherein said overcoat layer is elastically deformable to allow for movement of said fluid within said cavity during deployment, wherein the fluid filled cavity is arranged to deform upon insertion of said catheter shaft into the urethra, whereby at least a portion of said fluid filled cavity at said proximal end is arranged to be compressed to a smaller diameter, and upon continued insertion of said catheter shaft through the urethra into at least a bladder neck, at least said portion of said fluid filled cavity at said proximal end being arranged to expand back toward a greater diameter, as the fluid of said fluid filled cavity at said distal end is caused to flow toward the proximal end of the fluid filled cavity;
    a valve arranged to set the internal lumen of the catheter shaft in an open or closed state, the valve being a quarter-turn ball valve, comprising a hollow, perforated and pivoting ball to control flow through it, the ball being spherical or cylindrical, and the valve being open when the ball's hole is in line with the flow and closed when the ball's hole is pivoted 90 degrees, the valve being arranged at, or in a vicinity of, the distal discharge opening; and a valve handle or actuator arranged to bring the valve to an opened state upon activation, the valve handle extending as an arm towards only one side or in two opposite directions.

11. The urinary catheter of claim 10, wherein said at least one proximal drainage opening is arranged farther from said distal discharge opening than said proximal end of the deformable fluid filled cavity.

12. The urinary catheter of claim 10, wherein said at least one proximal drainage opening is arranged at a part of said catheter shaft over which said overcoat layer extends.

13. The urinary catheter of claim 1, wherein the valve is arranged to remain open when the valve actuator or handle is in a first state, and to remain closed when the valve handle or actuator is in a second state.

14. The urinary catheter of claim 10, wherein the valve is arranged at or in a vicinity of the distal discharge opening.

15. The urinary catheter of claim 10, wherein the valve is controllable with a handle, which is non-removably connected to the valve.

16. The urinary catheter of claim 10, wherein the catheter shaft comprises a closed proximal tip.

\* \* \* \* \*